(12) United States Patent
Ogawa

(10) Patent No.: US 11,763,457 B2
(45) Date of Patent: Sep. 19, 2023

(54) INFORMATION GENERATION METHOD, INFORMATION GENERATION APPARATUS, AND PROGRAM

(71) Applicant: Sony Group Corporation, Tokyo (JP)

(72) Inventor: Tetsu Ogawa, Tokyo (JP)

(73) Assignee: Sony Group Corporation, Tokyo (JP)

( * ) Notice: Subject to any disclaimer, the term of this patent is extended or adjusted under 35 U.S.C. 154(b) by 21 days.

(21) Appl. No.: 16/482,620

(22) PCT Filed: Dec. 6, 2017

(86) PCT No.: PCT/JP2017/043823
§ 371 (c)(1),
(2) Date: Jul. 31, 2019

(87) PCT Pub. No.: WO2018/150691
PCT Pub. Date: Aug. 23, 2018

(65) Prior Publication Data
US 2020/0013166 A1 Jan. 9, 2020

(30) Foreign Application Priority Data
Feb. 15, 2017 (JP) .................................. 2017-026458

(51) Int. Cl.
*G06T 7/00* (2017.01)
*A01G 7/00* (2006.01)
(Continued)

(52) U.S. Cl.
CPC .............. *G06T 7/0016* (2013.01); *A01G 7/00* (2013.01); *G01N 21/27* (2013.01);
(Continued)

(58) Field of Classification Search
CPC combination set(s) only.
See application file for complete search history.

(56) References Cited

U.S. PATENT DOCUMENTS

| 6,178,253 B1 | 1/2001 | Hendrickson et al. |
| 9,943,046 B2 * | 4/2018 | Bermudez Rodriguez .................. A01G 25/092 |

(Continued)

FOREIGN PATENT DOCUMENTS

| CN | 102564593 A | 7/2012 |
| CN | 102706328 A | 10/2012 |

(Continued)

OTHER PUBLICATIONS

International Search Report and Written Opinion for PCT/JP2017/043823.

(Continued)

*Primary Examiner* — Zhiyu Lu
(74) *Attorney, Agent, or Firm* — Michael Best & Friedrich LLP

(57) ABSTRACT

A specific environmental stress on vegetation is calculated highly accurately and relatively easily. For generation of environmental stress information, vegetation information is obtained first using an imaging signal of vegetation. Furthermore, reference vegetation information associated with vegetation information in a state of being free of, for example, a specific environmental stress is obtained. Moreover, as information associated with an environmental stress on the vegetation, difference information between vegetation information acquired from an imaging signal of vegetation in a state of being likely to have the specific environmental stress and the reference vegetation information is obtained.

20 Claims, 18 Drawing Sheets

(51) Int. Cl.
*G01N 21/27* (2006.01)
*G01N 21/64* (2006.01)
*G01N 33/00* (2006.01)

(52) U.S. Cl.
CPC ..... *G01N 21/6486* (2013.01); *G01N 33/0098* (2013.01); *G06T 7/97* (2017.01); *G06T 2207/10032* (2013.01); *G06T 2207/20224* (2013.01); *G06T 2207/30188* (2013.01)

(56) References Cited

U.S. PATENT DOCUMENTS

| | | | |
|---|---|---|---|
| 2008/0304711 A1 | 12/2008 | Scharf et al. | |
| 2010/0115830 A1* | 5/2010 | Dube | G01N 21/6486 356/402 |
| 2015/0027043 A1 | 1/2015 | Redden | |
| 2015/0027044 A1* | 1/2015 | Redden | A01M 21/043 47/58.1 R |
| 2016/0202679 A1* | 7/2016 | Bermudez Rodriguez | G05B 15/02 700/284 |
| 2017/0084039 A1* | 3/2017 | Ritter | G06T 7/11 |
| 2017/0118925 A1* | 5/2017 | Noguchi | G01J 3/42 |
| 2019/0018402 A1* | 1/2019 | Enomoto | G05B 23/024 |

FOREIGN PATENT DOCUMENTS

| | | | | |
|---|---|---|---|---|
| CN | 102788752 A | | 11/2012 | |
| CN | 106323880 A | | 1/2017 | |
| JP | 2015204788 A | | 11/2015 | |
| JP | 2016049102 A | | 4/2016 | |
| JP | 2016211899 A | | 12/2016 | |
| KR | 101415933 | * | 7/2014 | ............ G06Q 50/02 |
| WO | 2012/063455 A1 | | 5/2014 | |
| WO | WO2014073783 | * | 5/2014 | ........... G06V 20/188 |

OTHER PUBLICATIONS

International Preliminary Report on Patentability for PCT/JP2017/043823.
Extended European Search Report dated Dec. 20, 2019 for corresponding European Application No. 17896604.0.
Chinese Office Action dated Feb. 18, 2021 for corresponding Chinese Application No. 201780085949.8.

* cited by examiner

FIG.15
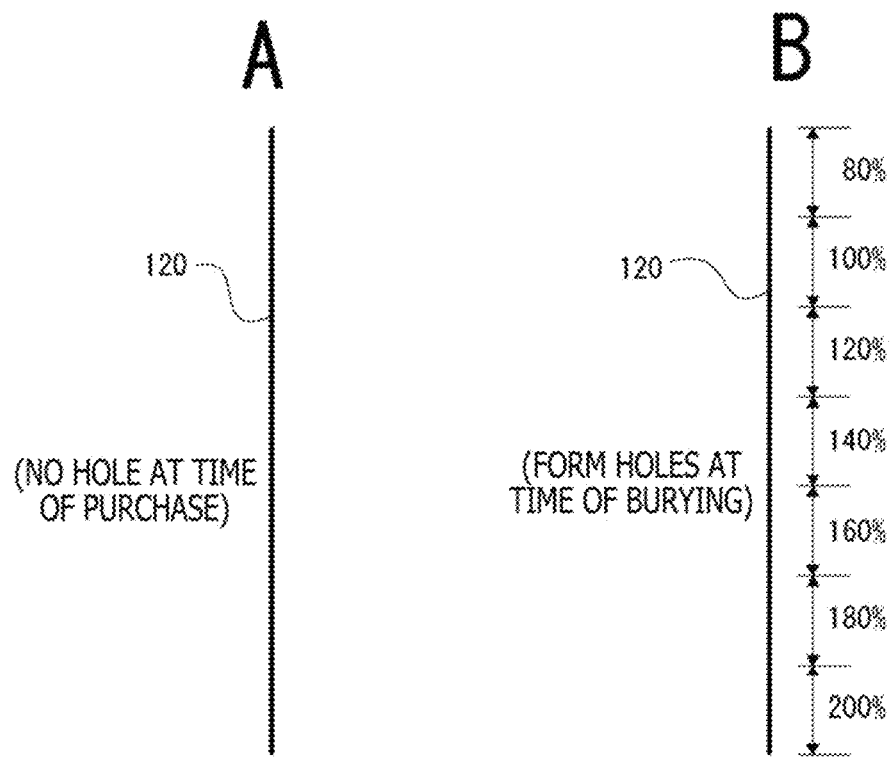
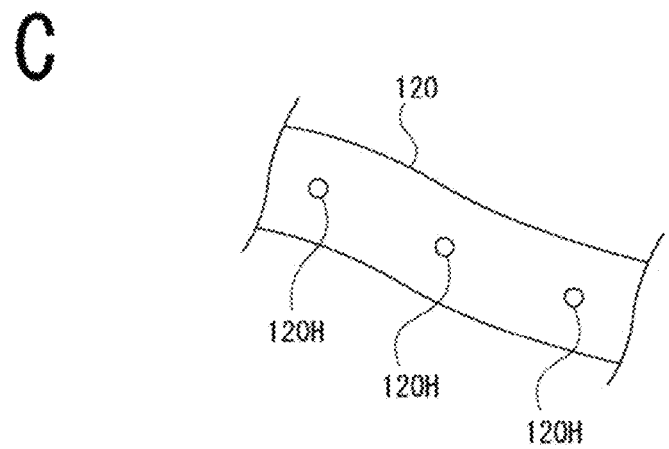

INFORMATION GENERATION METHOD, INFORMATION GENERATION APPARATUS, AND PROGRAM

TECHNICAL FIELD

The present technique relates to an information generation method and an information generation apparatus for generating information associated with a specific environmental stress on vegetation, and a program for realizing the information generation method and the information generation apparatus.

BACKGROUND ART

The photosynthetic activity of a plant and the growth of a plant body accompanying the photosynthetic activity are affected by an environmental state including the sunshine, a temperature, a saturation deficit, a $CO_2$ concentration, a soil moisture, and fertilizer components in a soil, and indicate different behaviors depending on a type of the plant and a state of acclimation to the environment even in the same environmental state.

Therefore, for favorable nurturing of the plant, it is important to grasp the environmental state, monitor the internal state of the plant involving a temporal change per type of the plant or per nurturing stage, and control a nurturing environment in response to the internal state.

PTL 1 mentioned below discloses, as a water stress spectroscopic measurement scheme, measuring a water stress by deriving a correlation from spectroscopic measurement and physical measurement of a water potential.

PTL 2 discloses using movement of a change point of a spectral reflectance from red visible light region to a near-infrared region as a water stress measurement method.

PTL 3 discloses imaging a reference district and a neighboring field in such a manner that the reference district overlaps the neighboring field by remote sensing, and correcting crop information associated with the neighboring field by imaging information and crop information (by an on-the-spot survey using a handheld measuring instrument) associated with the reference district.

CITATION LIST

Patent Literature

[PTL 1]
Japanese Patent No. 5186635
[PTL 2]
Japanese Patent No. 4524473
[PTL 3]
Japanese Patent No. 5162890

SUMMARY

Technical Problems

Meanwhile, in general, it is quite difficult to promptly and accurately monitor the internal state of a plant. For example, a state in which the plant is unable to sufficiently perform photosynthesis at an extremely low temperature even with the sufficient sunshine is determined from past experience or is difficult to discriminate unless a result indicating that several days pass with the state kept unchanged and the growth is not sufficient can be observed.

In addition, particularly in an outdoor environment or the like where an environmental condition is not fixed and a plurality of environmental stresses occurs, it is difficult to specify and quantify the environmental condition that affects the nurturing of the plant or to take measures in response to the state.

For example, even with the use of the technique described in each of the Patent Literatures, it is difficult to discriminate and observe a specific environmental stress in a case in which a plurality of stresses is likely to occur simultaneously.

Furthermore, a reduction in a quantity of irrigation water originating from a water shortage caused by drought and a reduction in fertilizers originating from the environmental pollution are desired.

For example, the quantity of irrigation water can be appropriately set if a soil moisture content can be measured with a soil moisture sensor; however, the measurement and setting require a high cost and cannot be achieved yet in a wide farm field.

While the spectroscopic measurement of the plant by imaging the plant with a camera can be realized at a low cost, the measurement is indirect measurement in the form of an environmental stress reaction of the plant; thus, in a case of simultaneous occurrence of a plurality of environmental stresses in a farm field, it is impossible to discriminate a cause (for example, a water shortage) of the environmental stresses. For example, in the case of reducing the quantity of irrigation water, it is impossible to understand whether the growth is adversely affected by the water shortage or by the other environmental stress; thus, it is difficult to determine an appropriate reduction in the quantity of irrigation water.

An object of the present technique is, therefore, to make it possible to grasp a specific environmental stress relatively easily even in an environment where a plurality of environmental stresses is likely to occur simultaneously.

Solution to Problems

An information generation method according to the present technique is a method of generating information associated with an environmental stress on vegetation. Furthermore, the information generation methods includes: a vegetation information acquisition procedure of acquiring vegetation information using an imaging signal of vegetation; and a difference acquisition procedure of acquiring difference information between the vegetation information and reference vegetation information related to a specific environmental stress.

While a plurality of environmental stresses on vegetation is present, information associated with a certain specific environmental stress is calculated. In a state, for example, in which stresses such as a temperature status and a drying status are generally the same, the information associated with the specific environmental stress (for example, a water stress) is calculated. To this end, a difference between reference vegetation information in a state of being free of the specific environmental stress and vegetation information in a state of being likely to have the specific environmental stress is obtained, and this difference is assumed as the information associated with the specific environmental stress.

It is conceivable in the information generation method described above that the vegetation information acquisition procedure includes obtaining vegetation information associated with a reference district set into the state of being free of the specific environmental stress from an imaging signal of the reference district, and obtaining vegetation information associated with a district to be measured set into the state of being likely to have the specific environmental stress from an imaging signal of the district to be measured, the reference vegetation information acquisition procedure includes calculating the reference vegetation information using the vegetation information associated with the reference district, and the difference acquisition procedure includes performing computation of a difference between the vegetation information associated with the district to be measured and the reference vegetation information.

For example, part of a farm field is assumed as the reference district. The reference district is assumed, for example, in a state of water stress-free. The other part of the farm field is assumed as the district to be measured, and the district to be measured is assumed in a state of having different irrigation conditions. In addition, the information associated with the specific environmental stress is calculated on the basis of imaging signals of those districts.

In the information generation method described above, it is conceivable that the reference district is provided in a location apart from the district to be measured.

The farm field is divided into, for example, the reference district and the district to be measured.

In the information generation method described above, it is conceivable that the reference district is provided to be adjacent to each district to be measured.

In other words, a district in the state of being free of the specific environmental stress is prepared in part of the district to be measured and this district is assumed as the reference district.

In the information generation method described above, it is conceivable that the reference vegetation information acquisition procedure includes calculating the reference vegetation information used to perform the computation of the difference between the vegetation information associated with the district to be measured and the reference vegetation information by using vegetation information obtained from an imaging signal of the reference district that is determined to be identical in a time zone to the imaging signal used for obtaining the vegetation information associated with the district to be measured.

The district to be measured and the reference district can be imaged in the same time zone in some cases, and cannot be imaged in the same time zone in other cases, depending on mechanical equipment circumstances such as the number of imaging apparatuses, a type, and a performance of the imaging apparatus and circumstances such as dimensions of a farm. If the district to be measured and the reference district are imaged in different time zones, changing environmental conditions such as a sunshine condition and a temperature causes a change in the conditions other than the specific environmental stress to be calculated. To address the problem, vegetation information for calculating the reference vegetation information is selected using imaging date information added to each imaging signal.

In the information generation method described above, it is conceivable that the vegetation information acquisition procedure includes obtaining vegetation information from a first imaging signal indicating the district to be measured imaged when the district to be measured is set into the state of being free of the specific environmental stress, and obtaining vegetation information from a second imaging signal indicating the district to be measured imaged when the district to be measured is set into the state of being likely to have the specific environmental stress, the reference vegetation information acquisition procedure includes calculating the reference vegetation information using the vegetation information obtained from the first imaging signal, and the difference acquisition procedure includes performing the computation of the difference between the vegetation information obtained from the second imaging signal and the reference vegetation information.

For example, for the farm field as the district to be measured, variable control is set to be capable of being exercised over a state of the specific environmental stress. In addition, the reference vegetation information is generated on the basis of the first imaging signal at the time of being free of the specific environmental stress. The difference between this reference vegetation information and the vegetation information obtained from the second imaging signal at the time of applying the specific environmental stress is computed.

In the information generation method described above, it is conceivable that the imaging signal is a captured image.

Furthermore, in the information generation method described above, it is conceivable that the difference acquisition procedure includes generating image information serving as the difference information.

For example, image information representing the difference between the vegetation information acquired from the captured image of vegetation in the state of being likely to have the specific environmental stress and the reference vegetation information is generated.

In the information generation method described above, it is conceivable that the reference vegetation information acquisition procedure includes calculating an average value of vegetation information in the state of being free of the specific environmental stress in calculating the reference vegetation information.

The vegetation information obtained from the captured images in the state of being free of the specific environmental stress have unevenness to some extent. To address the problem, reference vegetation information that serves as a representative value of the vegetation information is obtained using a value acquired by computing the average value.

In the information generation method described above, it is conceivable that the specific environmental stress is any one of a water stress, a low-temperature stress, a high-temperature stress, a drying stress, a stress caused by a shortage of carbon dioxide, or a nitrogen stress.

Furthermore, in the information generation method described above, it is conceivable that the vegetation information is any one of a PRI, a magnitude of chlorophyll fluorescence, a chlorophyll fluorescence index, or a state transition reflectance.

An information generation apparatus according to the present technique includes: a vegetation information acquisition section that acquires vegetation information using an imaging signal of vegetation; and a difference acquisition section that acquires difference information between the vegetation information and reference vegetation information related to a specific environmental stress.

In addition, the information generation apparatus further includes a reference vegetation information acquisition section that obtains the reference vegetation information using vegetation information acquired from an imaging signal of the vegetation in a state of being free of the specific environmental stress.

This information generation apparatus can obtain the reference vegetation information with the state of being free of the specific environmental stress which is, for example, the water stress assumed as a reference, and obtain the difference between the vegetation information acquired from the imaging signal in the district in which the specific environmental stress, for example, is likely to occur and the reference vegetation information.

It is conceivable that the information generation apparatus described above further includes an image acquisition section that acquires captured image data as an imaging signal by an external imaging apparatus.

In other words, the image acquisition section acquires captured images of vegetation captured by the external imaging apparatus as data for use in a stress measurement process.

In the information generation apparatus described above, it is conceivable that for the captured image data acquired by the image acquisition section, the information generation apparatus includes a division acquisition section that acquires division information for discriminating a captured image indicating the vegetation information in the state of being free of the specific environmental stress from a captured image indicating vegetation information in a state of being likely to have the specific environmental stress.

The division acquisition section acquires information, for example, for discriminating whether the captured image is an image of the reference district or an image of the district to be measured.

In the information generation apparatus described above, it is conceivable that the reference vegetation information acquisition section determines vegetation information obtained from the captured image indicating the vegetation information in the state of being free of the specific environmental stress on the basis of the division information, and obtains the reference vegetation information using the determined vegetation information.

It is thereby possible to appropriately select the vegetation information in the state of being free of the specific environmental stress and obtain the reference vegetation information.

In the information generation apparatus described above, it is conceivable that for the captured image data acquired by the image acquisition section, the information generation apparatus includes an image division section that divides the captured image data into a captured image indicating vegetation information in the state of being free of the specific environmental stress and a captured image indicating vegetation information in a state of being likely to have the specific environmental stress.

In a case, for example, in which one captured image contains a mixture of an image of the reference district and an image of the district to be measured, the images of those districts are divided and extracted.

In the information generation apparatus described above, it is conceivable that the reference vegetation information acquisition section calculates the reference vegetation information relative to vegetation information in a state of being likely to have the specific environmental stress by using vegetation information obtained from an imaging signal in the state of being free of the specific environmental stress, the imaging signal being determined to be identical in a time zone to an imaging signal used for obtaining the vegetation information in the state of being likely to have the specific environmental stress.

For example, the reference vegetation information relative to the vegetation information obtained from the imaging signal of the district to be measured is calculated using the vegetation information obtained from the imaging signal of the reference district imaged in the same time zone as that of the imaging signal of the district to be measured.

It is conceivable that the information generation apparatus described above includes an instruction section that issues an instruction to change a farm field into a state of being free of the specific environmental stress or a state of being likely to have the specific environmental stress.

For example, irrigation installation is controlled so that a certain farm field can be changed into a state of being likely to have the water stress or a state of being free of the water stress.

It is conceivable that the information generation apparatus described above includes an instruction section that controls environmental stress variable installation on a basis of the difference information acquired by the difference acquisition section.

For example, automatic control or the like is set to be capable of being exercised over a valve or the like that regulates a quantity of irrigation on a basis of the difference information between the vegetation information and the reference vegetation information.

In the information generation apparatus described above, it is conceivable that the difference acquisition section generates image information serving as the difference information, and the information generation apparatus includes an image output section that outputs the image information.

For example, an image indicating the difference information is output to correspond to the farm field (district to be measured).

In the information generation apparatus described above, it is conceivable that the reference vegetation information acquisition section obtains the reference vegetation information using the vegetation information acquired by the vegetation information acquisition section from the imaging signal of the vegetation in the state of being free of the specific environmental stress. In other words, the difference information is obtained with the vegetation in the state of being free of the environmental stress as the reference.

Advantageous Effects of Invention

According to the present technique, it is possible to grasp a specific environmental stress in an environment such as an outdoor farm field where a plurality of environmental stresses is likely to occur simultaneously, and to optimize discrimination of causes of the environmental stresses and crop management using a result of discrimination.

It is noted that effects are not always limited to those described herein but may be any of the effects described in the present disclosure.

BRIEF DESCRIPTION OF DRAWINGS

FIG. 15 is an explanatory diagram in a case of changing a quantity of irrigation stepwise by an irrigation tube according to the embodiments.

DESCRIPTION OF EMBODIMENTS

Embodiments will be described hereinafter in the following order.
<1. First embodiment>
<2. Second embodiment>
<3. Third embodiment>
<4. Fourth embodiment>
<5. Setting of quantity of irrigation>
<6. Detection of damage in irrigation channel>
<7. Measurement of other environmental stress>
<8. Conclusion and modifications>

1. First Embodiment

Figure 1:
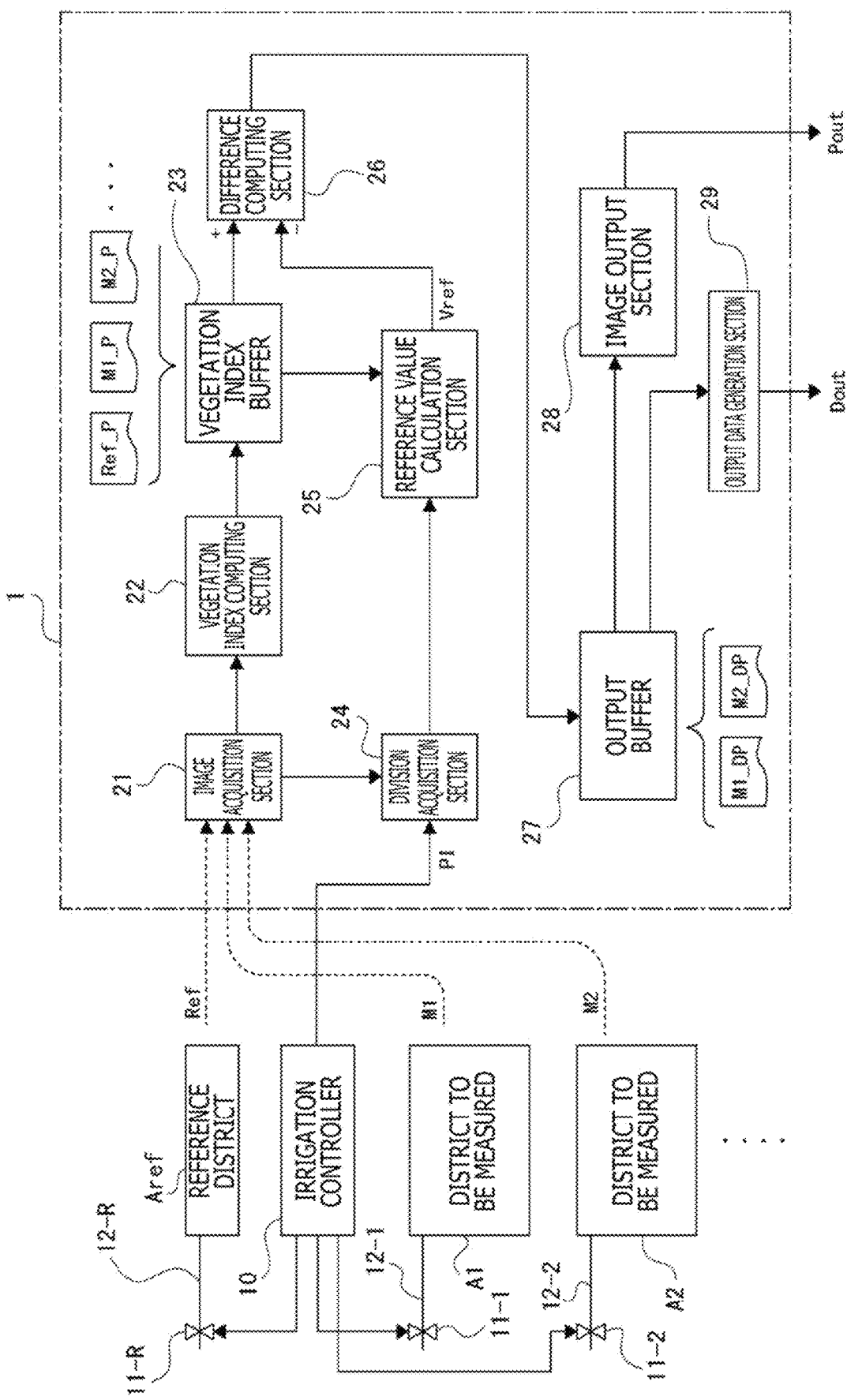
FIG. 1 is an explanatory diagram of a system configuration according to a first embodiment of the present technique.

FIG. 1 depicts a system configuration including an information generation apparatus 1 that calculates a specific environmental stress on vegetation as a first embodiment.

The information generation apparatus 1 calculates the specific environmental stress using captured images that are imaging signals about a field to be calculated.

It is noted that a case of measuring a water stress as the specific environmental stress will be described in each embodiment by way of example.

FIG. 1 depicts a reference district Aref and districts to be measured $A_1$, A2, and the like as an example of a farm field. The reference district Aref and the districts to be measured A1, A2, and the like are in the farm field where plants/agricultural crops are cultivated. The farm field is divided into districts to calculate an environmental stress. For example, the farm field is divided into the districts in units of irrigation installation.

Figure 2:
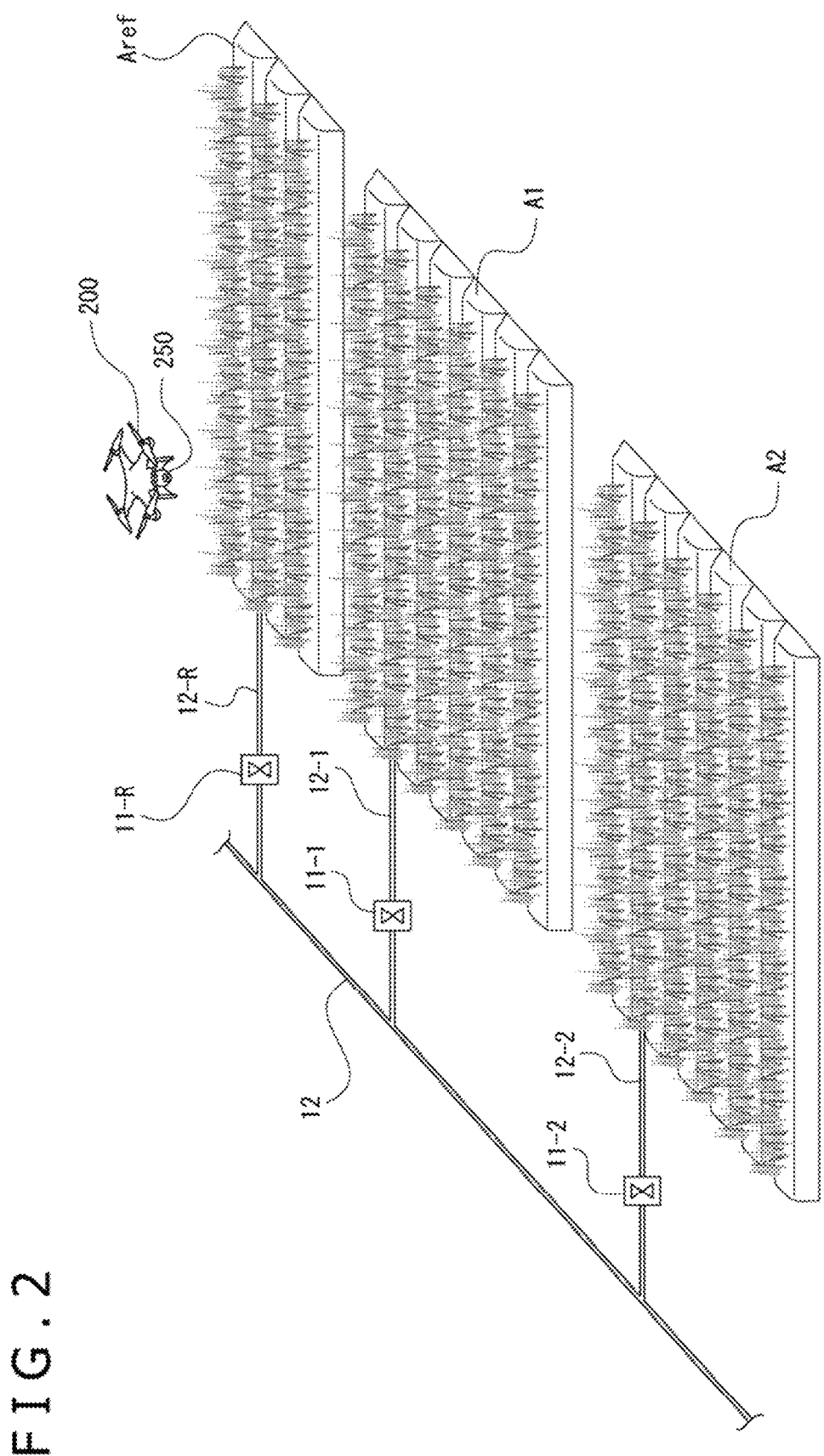
FIG. 2 is an explanatory diagram of districts in a farm field set in the embodiment.

FIG. 2 depicts a state of the farm field. In the farm field, water supplied by an irrigation channel 12 is introduced to irrigation setting valves 11 (11-R, 11-1, 11-2, and the like) in the districts.

In the reference district Aref, an irrigation channel 12-R by an irrigation tube, for example, is drawn, and a quantity of irrigation water of the irrigation channel 12-R is controlled by the irrigation setting valve 11-R.

Furthermore, in the districts to be measured A1, A2, and the like, irrigation channels 12-1, 12-2, and the like by irrigation tubes, for example, are similarly drawn, respectively. Quantities of irrigation water of the irrigation channels 12-1, 12-2, and the like are controlled by the irrigation setting valves 11-1, 11-2, and the like, respectively.

In this way, the quantities of irrigation water can be individually set in the reference district Aref and the districts to be measured A1, A2, and the like. In other words, states of the water stress can be individually set in the districts.

FIG. 2 depicts a small-sized air vehicle 200. The air vehicle 200 can move high above the farm field by, for example, operator's radio control or radio autopilot. In addition, the air vehicle 200 mounts therein an imaging apparatus 250, so that the air vehicle 200 can image vegetation in the reference district Aref and the districts to be measured A1 and A2 while moving high above the farm field.

FIG. 1 schematically depicts the reference district Aref and the districts to be measured A1 and A2 as depicted in FIG. 2. It is noted that areas, disposition, and the like of the reference district Aref and the districts to be measured A1 and A2 are given as an example. A way of division into the districts, area ratios, and the like are not particularly limited.

An irrigation controller 10 is an apparatus that controls quantities of released water by the irrigation setting valves 11 (11-R, 11-1, 11-2, and the like).

In this example, the irrigation controller 10 is capable of not only controlling each quantity-of-irrigation setting valve 11 in response to an operator's instruction or the like but also supplying information associated with the quantity of released water by the quantity-of-irrigation setting valve 11 to the information generation apparatus 1 as division information PI.

The reference district Aref refers herein to a district in which a sufficient quantity of irrigation water is set to prevent a water shortage regardless of other environmental conditions such as weather. In other words, the reference district Aref is the district set in a state of water stress-free.

Therefore, the reference district Aref depicted in FIG. 1 and the like is the district in which the irrigation controller 10 controls the irrigation setting valve 11 to ensure sufficient irrigation. While this reference district Aref may be set as a fixed location, the reference district Aref may be the district solely controlled into the state of water stress-free at a time of calculating the environmental stress, and the reference district Aref may be changed.

On the other hand, the districts to be measured A1, A2, and the like are defined as districts in each of which a quantity of irrigation is set as minimum as possible per location, per weather, or per nurturing stage. Therefore, the districts to be measured A1, A2, and the like are the districts in each of which the irrigation controller 10 controls the irrigation setting valve 11 so that the quantity of irrigation water is restricted to some extent.

This enables the information generation apparatus 1 to discriminate what district (district with what irrigation setting valve 11) is the reference district Aref or what district is the district to be measured A1 or A2 by supplying information associated with the quantity of irrigation water (control information of the irrigation setting valve 11) in each district from the irrigation controller 10 to the information generation apparatus 1 as the division information PI.

It is noted that each quantity-of-irrigation setting valve 11 may be structured to manually regulate the quantity of released water. In that case, the irrigation controller 10 is not always provided. In addition, in that case, it is conceivable that the division information PI is manually input to the information generation apparatus 1 by a staffer who set the quantity of irrigation water in each district.

The information generation apparatus 1 has an image acquisition section 21, a vegetation index computing section 22, a vegetation index buffer 23, a division acquisition section 24, a reference value calculation section 25, a difference computing section 26, an output buffer 27, an image output section 28, and an output data generation section 29.

It is noted that these sections may be each configured with hardware or may be each a function realized by software (an environmental stress information generation program) in a computer apparatus to be described later. An example in which each of these sections is realized as a functional block by the software will be described hereinafter.

The image acquisition section 21 acquires image data obtained by, for example, the imaging apparatus 250 mounted in the air vehicle 200 described above as images for use in calculating the environmental stress.

In addition, the image acquisition section 21 acquires an image file Ref as image data obtained by imaging the vegetation in at least the reference district Aref, and image files M1, M2, and the like as image data obtained by imaging the vegetation in the districts to be measured A1, A2, and the like.

It is noted that the acquired image files (Ref, M1, M2, and the like) are image data files transmitted from the imaging apparatus 250 or a relay apparatus over wired transmission or wireless transmission and received by the information generation apparatus 1, or image data files recorded in a recording medium by the imaging apparatus 250 side or the other recording apparatus and acquired by reproducing the recording medium by the information generation apparatus 1.

Furthermore, the image acquisition section 21 may acquire the captured image files (Ref, M1, M2, and the like) in real time (at a time of imaging) or at later timing. The image acquisition section 21 may acquire images in the reference district Aref and the districts to be measured A1, A2, and the like at least at timing of generating environmental stress information.

Moreover, while the imaging apparatus 250 mounted in the air vehicle 200 is mentioned as an example of the imaging apparatus for acquiring the captured images, the image acquisition section 21 may acquire captured images by fixed point cameras installed in the farm field or images captured using an imaging apparatus owned by a person.

Furthermore, it is assumed in the present embodiment that the image files (Ref, M1, M2, and the like) acquired by the image acquisition section 21 contain spectroscopic measurement images. In other words, the imaging apparatus 250 is assumed as a multispectral camera and the image files (Ref, M1, M2, and the like) contain measurement images at arbitrary two or more wavelengths.

Figure 3:
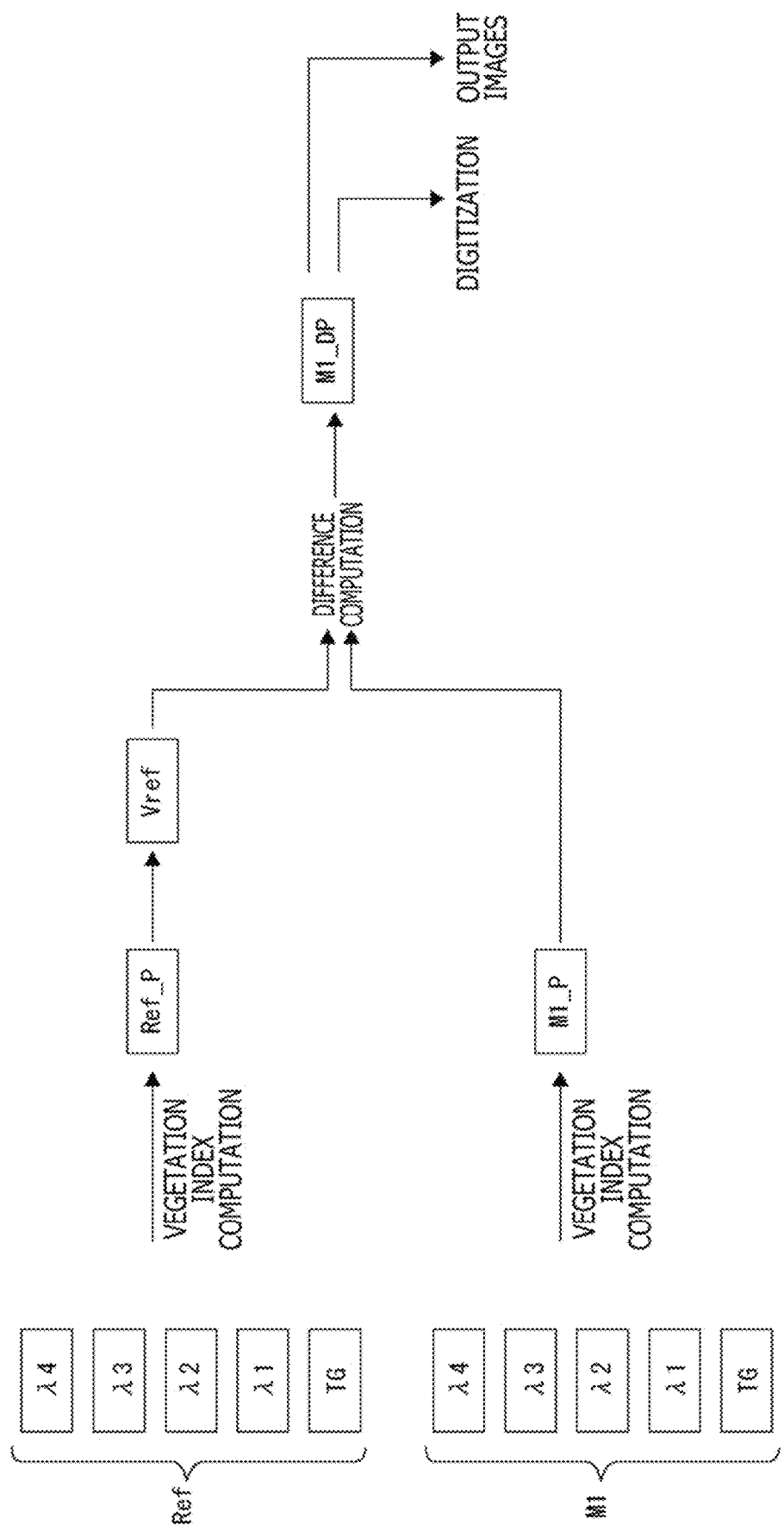
FIG. 3 is an explanatory diagram of a flow of calculation of environmental stress information according to the embodiment.

FIG. 3 depicts an example of data contained in the image files Ref and M1. Each of these image files contains images at a plurality of wavelengths denoted by "λ1," "λ2," "λ3," and "λ4." While four images are depicted herein, each image file is assumed to contain images at least two wavelengths.

Furthermore, tag information TG is added to each image file. The tag information TG contains imaging date information, position information (longitude/latitude information) as GPS (Global Positioning System) data, imaging apparatus information (individual identification information, model information, and the like associated with the camera), information associated with each image data (information such as image sizes, wavelengths, and imaging parameters), and the like.

The vegetation index computing section 22 in the information generation apparatus 1 of FIG. 1 performs a process for obtaining a vegetation index that serves as information associated with vegetation using the images acquired by the image acquisition section 21.

Examples of the index computed by the vegetation index computing section 22 as an index for use in measuring the environmental stress include:
PRI (photochemical reflectance index)
Magnitude of chlorophyll fluorescence
Chlorophyll fluorescence index
State transition reflectance,
and the like.

The magnitude of chlorophyll fluorescence may be a magnitude of chlorophyll fluorescence excited by solar light (solar-induced chlorophyll fluorescence (SIF)) or excited not by the solar light but by using a laser or an LED.

The chlorophyll fluorescence index is for measuring the chlorophyll fluorescence at several separate wavelengths and is represented by a ratio of two wavelengths, for example, 685 nm and 735 nm.

In the present embodiment, a case of obtaining the PRI will be described by way of example.

The PRI is obtained by indexing a spectral reflectance that changes with de-epoxidation of a xanthophyll cycle. The xanthophyll cycle is a mechanism that releases, as heat, excessive light energy that is too much in amount to be consumed by a photosynthetic reaction due to stomatal closure accompanying strong light or the water stress.

The PRI is assumed herein to be calculated as follows.

$$PRI=(R570-R531)/(R570+R531)$$

It is noted that "R570" denotes a reflected-light intensity at a wavelength of 570 nm and "R531" denotes a reflected-light intensity at a wavelength of 531 nm.

Therefore, the vegetation index computing section 22 generates vegetation index image files Ref_P, M1_P, M2_P, and the like based on PRI values using the images at the wavelength of 570 nm and the images at the wavelength of 531 nm in the image files Ref, M1, M2, and the like.

In FIG. 3, generating the vegetation index image file Ref_P from the image file Ref and generating the vegetation index image file M1_P from the image file M1 are depicted.

In other words, these vegetation index image files are obtained using "λ1" images (for example, images at the wavelength of 570 nm) and "λ2" images (for example, images at the wavelength of 531 nm). The vegetation index computing section 22 computes the PRI for a value of each pixel configuring each image (luminance value in response to the reflected-light intensity) and obtains a PRI value of each pixel as a vegetation index image. A file containing image data about the PRI value of each pixel serves as a vegetation index image file.

It is noted that in a case of the PRI values defined above, the PRI values also increase with an increase in stress.

These vegetation index image files obtained by the vegetation index computing section 22 are temporarily stored in the vegetation index buffer 23.

The chlorophyll fluorescence as another index will be described complementally.

A stress can be also detected using the chlorophyll fluorescence. The chlorophyll fluorescence is fluorescence emitted from a plant accompanying photosynthesis in the plant, and is a phenomenon that energy is released as fluorescence at a wavelength of approximately 680 to 770 nm in a higher plant without dissipation of the energy within certain time from a reaction center where electrons are excited by light.

The released energy is 0.5% to 3% of input light energy, varies with a photosynthetic state of the plant, and increases in the case in which excessive light energy that is too much in amount to be consumed by a photosynthetic reaction due to stomatal closure accompanying strong light or water stress.

Each the PRI and the chlorophyll fluorescence is a reaction in which a change is observed within a few minutes in response to a stress.

Furthermore, an NDVI (Normalized Difference Vegetation Index) or the like may be used to discriminate a persistent stress that appears as a growth difference as a result even if an instantaneous stress cannot be discriminated.

The vegetation index computing section 22 may obtain the vegetation index image files based on values other than the PRI values using the acquired image files Ref, M1, M2, and the like.

The division acquisition section 24 in the information generation apparatus 1 acquires the division information PI as described above. This division information PI is information for distinguishing the vegetation index image files stored in the vegetation index buffer 23.

The division information PI is at least information for distinguishing what file is the vegetation index image file Ref_P corresponding to the reference district Aref or what file is the vegetation index image file M1_P, M2_P, or the like corresponding to the district to be measured A1, A2, or the like.

As described above, the division information PI is often supplied from the irrigation controller 10. Furthermore, the tag information TG in each of the image files (Ref, M1, M2, and the like) acquired by the image acquisition section 21 is often used as the division information PI. Moreover, information input by a staffer is often used as the division information PI although not depicted in FIG. 1.

The division acquisition section 24 supplies the division information PI or the information for file designation generated on the basis of the division information PI to the reference value calculation section 25.

The reference value calculation section 25 calculates reference vegetation information (a reference value Vref) for use in obtaining environmental stress information.

The reference value calculation section 25 calculates the reference value Vref using the vegetation index image file Ref_P. Owing to this, to calculate the reference value Vref, the reference value calculation section 25 selects and reads the vegetation index image file Ref_P corresponding to the reference district Aref from among the vegetation index image files stored in the vegetation index buffer 23 on the basis of the information from the division acquisition section 24.

The reference value calculation section 25 calculates the reference value Vref using the value of each pixel of the image data in the vegetation index image file Ref_P, that is, the PRI value of each section in the reference district Aref.

It is conceivable that the reference value Vref is set to, for example, an average value of the pixel values configuring each image in the vegetation index image file Ref_P. For example, an average value of all pixels is simply set as the reference value Vref.

Furthermore, while the process in the present embodiment are intended to measure the stress related to the plant, the captured image often contains a soil part. An image of the soil part, that is, pixel values of the vegetation index images corresponding to the soil part act as a noise for the PRI values of the plant.

Therefore, the reference value calculation section 25 may exclude the soil, extract only portions (pixels) in which the plant appear, obtain an average value of the PRI values of the extracted pixels, and use the obtained average value as the reference value Vref.

To discriminate a plant part from the soil part in the images, it is conceivable to use the other vegetation index (for example, NDVI).

Moreover, the reference value calculation section 25 may extract only portions where the plant is exposed to light, obtain an average value, and use the average value as the reference value Vref.

Alternatively, the reference value calculation section 25 may extract only portions of the plant that is not exposed to the light, obtain an average value, and use the average value as the reference value Vref.

These can be obtained by a scheme for discriminating the plant from the soil with, for example, the other vegetation index such as the NDVI and then selecting pixels at high luminances or selecting pixels at low luminances.

The difference computing section 26 calculates a stress value for each of the districts to be measured A1, A2, and the like using the reference value Vref calculated by the reference value calculation section 25 and the vegetation index image files M1_P, M1_P, and the like of the districts to be measured A1, A2, and the like stored in the vegetation index buffer 23.

In FIG. 3, generating stress information associated with the district to be measured A1 as a difference image file M1_DP obtained as a difference between the vegetation index image file M1_P and the reference value Vref is depicted.

Specifically, a difference value is obtained by subtracting the reference value Vref from each of the pixel values of the vegetation index image file M1_P, and the stress information associated with the district to be measured A1 is generated as image data containing this difference value as each pixel value as it is. This image data is defined as the difference image file M1_DP.

Similarly, a difference value is obtained by subtracting the reference value Vref from each of the pixel values of the vegetation index image file M2_P, and the stress information associated with the district to be measured A2 is generated as image data containing this difference value as each pixel value as it is. This image data is defined as a difference image file M2_DP.

The difference image files M1_DP, M2_DP, and the like that are the stress information obtained for the districts to be measured A1, A2, and the like are stored in the output buffer 27.

The difference image files M1_DP, M2_DP, and the like stored in the output buffer 27 are output from the image output section 28 as output image information Pout by, for example, staffer's operation. The output image information Pout is, for example, displayed on a monitor display, transmitted to the other information processing apparatus, or stored in a storage medium in a storage apparatus.

The output images are images each in response to the difference value per pixel obtained by the difference computing section 26. Therefore, the output images serve as images that express degrees of the water stress on the vegetation in respective sections for the districts to be measured A1, A2, and the like in which the water stress is likely to be present with reference to the water stress-free reference district Aref.

Furthermore, the difference image files M1_DP, M2_DP, and the like stored in the output buffer 27 may be processed by the output data generation section 29 in response to, for example, staffer's operation. For example, the output data generation section 29 may obtain an average value, a representative value, a maximum value, a minimum value, a center of gravity value, and the like of the pixel values of the difference image file M1_DP, and output these 0 as output data Dout that serves as an index of the water stress for the district to be measured A1.

Alternatively, the output data generation section 29 may further analyze difference values of the difference image file M1_DP, generate observation information associated with the water stress, a distribution status within the district to be measured A1, and other information, and output these pieces of information as the output data Dout. Using these pieces of information makes it possible to obtain diverse or advanced analysis information.

The information generation apparatus 1 according to the first embodiment configured as depicted in FIG. 1 and described so far measures an individual piece (reference district Aref) that serves as a reference on conditions different only in the specific environmental stress (water stress) to be calculated apart from the farm field to be measured, and calculates the environmental stress (water stress) on the vegetation from the difference.

Subtracting the reference value Vref that is a computation result, for example, the average value of the vegetation index in the reference district Aref in which irrigation is sufficiently performed to prevent occurrence of the water stress, from a computation result of the vegetation index in each district to be measured enables the information generation apparatus 1 to obtain the difference between the former individual piece and the other individual piece different in water stress.

At this time, setting measurement time (time at which the imaging apparatus 250 captures the images) to be substantially identical (same time zone) enables the other environmental stresses such as the temperature and the sunshine to be identical in condition. In other words, causing the air vehicle 200 to image the reference district Aref and the districts to be measured A1 and A2 in order in a short time makes it possible to regard the vegetation indexes (vegetation index image files Ref_P, M1_P, M2_P, and the like) calculated on the basis of the image files Ref, M1, M2, and the like captured at that time as the vegetation indexes identical in the other conditions and different only in the water stress.

Figure 4:
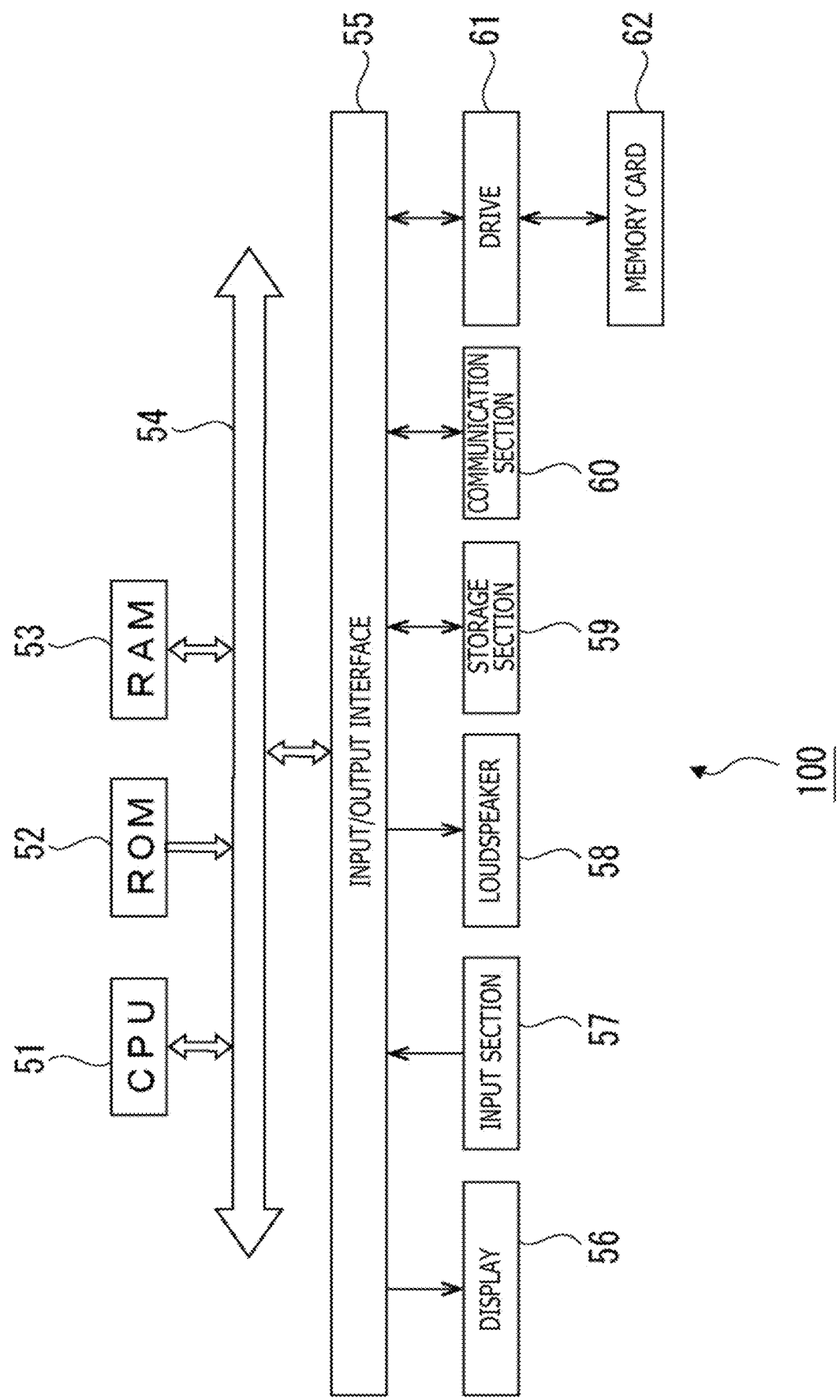
FIG. 4 is a block diagram of a computer apparatus that realizes an information generation apparatus according to the embodiment.

The information generation apparatus 1 having the functional configurations depicted in FIG. 1 and described so far is realized by a computer apparatus 100 having a hardware configuration depicted in, for example, FIG. 4.

As depicted in FIG. 4, the computer apparatus 100 is configured with a CPU (Central Processing Unit) 51, a ROM (Read Only Memory) 52, and a RAM (Random Access Memory) 53.

The CPU 51 executes various processes in accordance with a program stored in the ROM 52 or a program loaded from a storage section 59 to the RAM 53. The RAM 53 also stores data and the like necessary for the CPU 51 to execute the various processes as appropriate.

The CPU 51, the ROM 52, and the RAM 53 are mutually connected via a bus 54. An input/output interface 55 is also connected to this bus 54.

A display 56 including a liquid crystal panel, an organic EL panel, or the like, an input section 57 including a keyboard, a mouse, and the like, a loudspeaker 58, the storage section 59 configured with an HDD or the like, a communication section 60, and the like can be connected to the input/output interface 55.

The display 56 may be either integrated with the computer apparatus 100 or an apparatus separate from the computer apparatus 100. For example, the output images Pout and the output data Dout are displayed on the display 56.

The input section 57 means an input device used by a user who uses the computer apparatus 100.

The communication section 60 performs a communication process via a network including the Internet and holds communication with apparatuses in peripherals. For example, the communication section 60 is communicable with the imaging apparatus 250.

Furthermore, a drive 61 is connected to the input/output interface 55, a memory card 62 is attached thereto as needed, a computer program read from the memory card 62 is installed into the storage section 59 as needed, and data processed by the CPU 51 is stored in the storage section 59 as needed. Needless to say, the drive 61 may be a recording/reproducing drive for a removable storage medium such as a magnetic disk, an optical disk, or a magneto-optical disk.

With such a hardware configuration, the computer apparatus 100 can perform the processes as the information generation apparatus 1 according to the embodiment, that is, the processes as the image acquisition section 21, the vegetation index computing section 22, the division acquisition section 24, the reference value calculation section 25, the difference computing section 26, the image output section 28, and the output data generation section 29. In other words, these processes are realized by software activated in the CPU 51. A program that configures the software is downloaded from the network or read from a removable storage medium, and installed into the computer apparatus 100 of FIG. 4. Alternatively, the program may be stored in the HDD or the like that serves as the storage section 59 in advance. By activating the program in the CPU 51, the functions of the sections appear.

Moreover, the vegetation index buffer 23 and the output buffer 27 are realized using a storage area of, for example, the RAM 53.

The image files Ref, M1, M2, and the like are received by the communication section 60 or read from the storage medium by the drive 61, and stored in, for example, the storage section 59. The CPU 51 having the function as the image acquisition section 21 acquires image files necessary to generate the stress information among the image files captured in that way.

Similarly, the CPU 51 acquires the necessary division information PI. Alternatively, the division information PI is often captured as information input by an operator using the input section 57.

Output of information by the image output section 28 and the output data generation section 29 is executed in various forms including output to the display 56 or the loudspeaker 58 as images or voices, storage in the storage section 59, transmission by the communication section 60 to external apparatuses, and storage in the storage medium by the drive 61.

It is noted that the information processing apparatus 1 according to the embodiment is not limited to the configuration with the single information processing apparatus (computer apparatus) 100 having the hardware configuration depicted in FIG. 4 but may be configured by systematizing a plurality of computer apparatuses. The plurality of computer apparatuses may be systematized by a LAN or the like or may be disposed at remote locations by a VPN (Virtual Private Network) or the like using the Internet or the like. The plurality of computer apparatuses may include a computer apparatus available by a cloud computing service.

Furthermore, the computer apparatus 100 of FIG. 4 can be realized as a personal computer of a stationary type, a notebook type, or the like, or as a mobile terminal such as a tablet terminal or a smart phone. Moreover, an electronic apparatus such as a measurement apparatus, a television apparatus, a monitor apparatus, an imaging apparatus, or an installation management apparatus having the functions as the computer apparatus 100 may mount the information generation apparatus 1 according to the present embodiment.

An example of a stress information generation process performed by the information generation apparatus 1 will be described.

Figure 5:
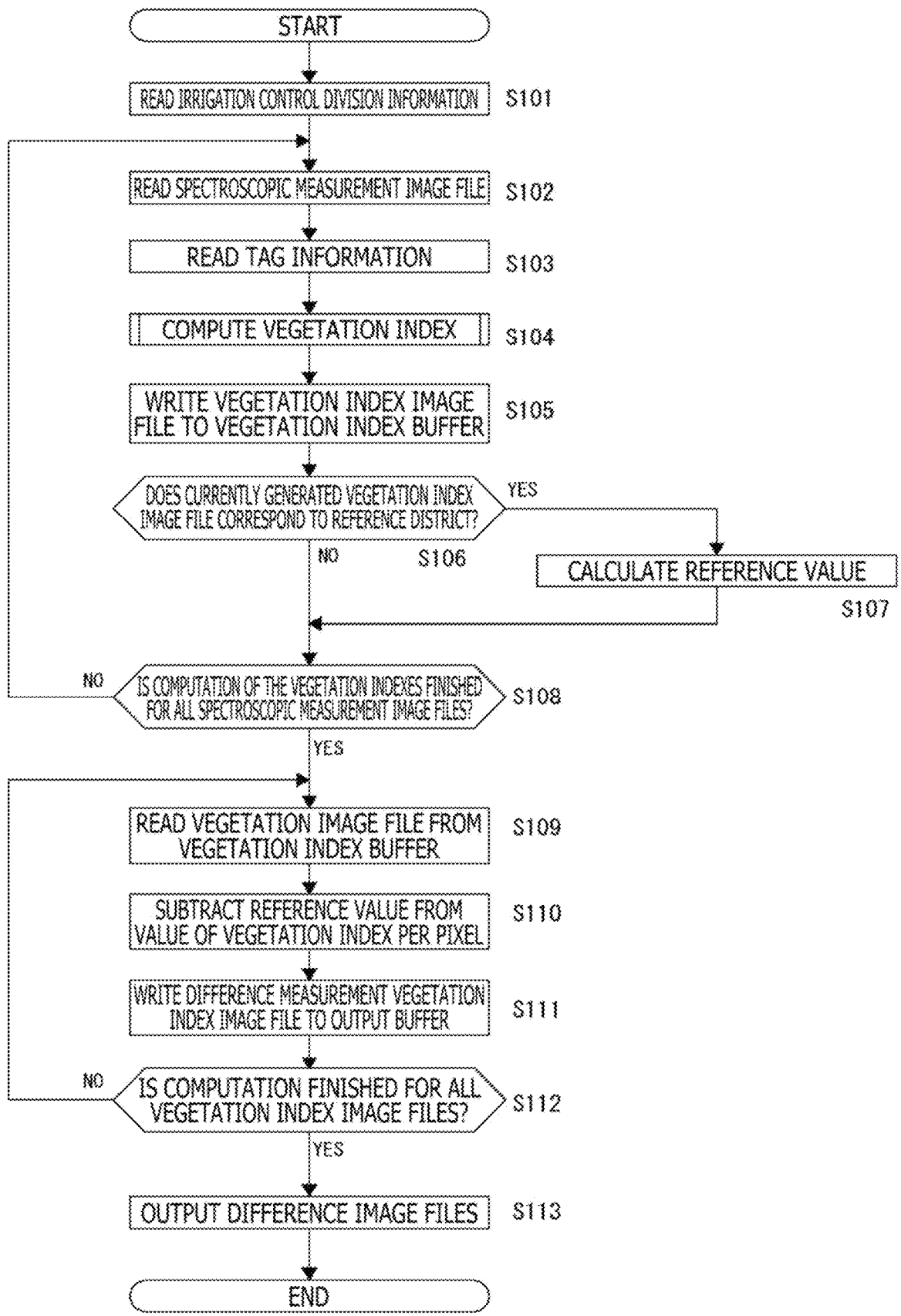
FIG. 5 is a flowchart of an environmental stress information generation process according to the embodiment.
Figure 6:
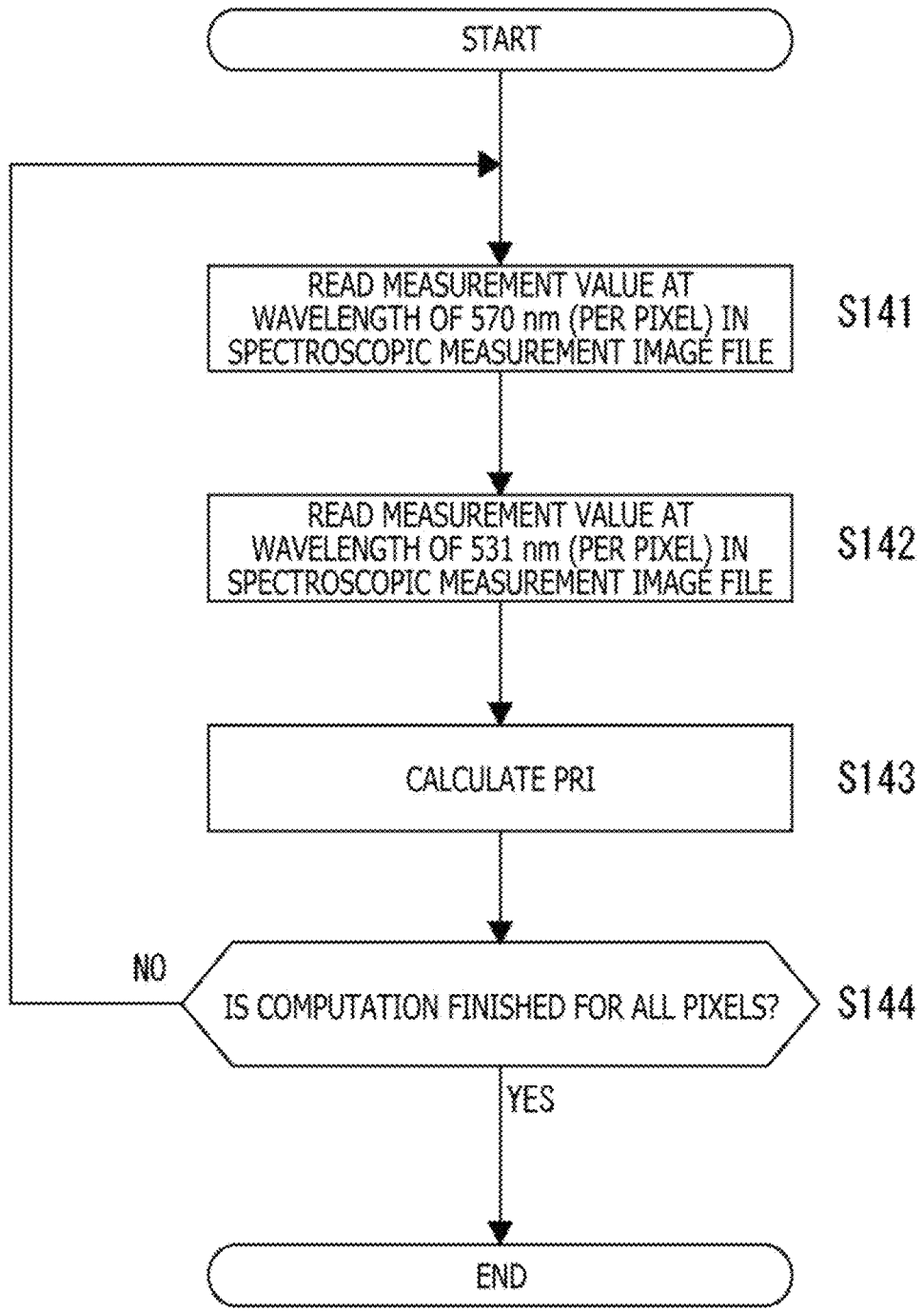
FIG. 6 is a flowchart of a computing process for a vegetation index according to the embodiment.

FIGS. 5 and 6 depict an example of the process performed by the CPU 51 in the computer apparatus 100 having the functions depicted in FIG. 1 as the information generation apparatus 1.

The CPU 51 reads the division information PI transmitted from, for example, the irrigation controller 10 in Step S101. In other words, the CPU 51 acquires the information for discriminating an irrigation control division, specifically, information for distinguishing the reference district Aref and the districts to be measured A1, A2, and the like from one another.

The CPU 51 reads the spectroscopic measurement image file for use in the process in Step S102. In other words, the image files Ref, M1, M2, and the like are the spectroscopic measurement image files to be processed as described above, and the CPU 51 reads one spectroscopic measurement image file (which is assumed, for example, as the image file Ref). Specifically, Step S102 is a process for reading the image file Ref among the image files Ref, M1, M2, and the like transmitted from the imaging apparatus 250 or the like and stored in the storage section 59 or the like.

The CPU 51 reads the tag information TG added to the read image file Ref in Step S103.

The tag information is used as information (division information PI) for distinguishing the reference district Aref and the districts to be measured A1, A2, and the like from one another as needed.

The CPU 51 computes the vegetation index on the basis of the image file Ref in Step S104. In a case of performing the process for this image file Ref, the CPU 51 obtains the vegetation index of the reference district Aref in Step S104.

FIG. 6 depicts an example of the process for computing this vegetation index (in the case of the PRI).

FIG. 6 depicts the process for generating one vegetation index image file from one image file. In other words, the CPU 51 performs the process of FIG. 6 for the image file Ref and generates the vegetation index image file Ref_P.

The CPU 51 reads a value of one pixel as a measurement value at the wavelength of 570 nm in the spectroscopic measurement image file (which is the image file Ref in this case) in Step S141 of FIG. 6.

Furthermore, the CPU 51 reads a value of one pixel as a measurement value at the wavelength of 531 nm in the spectroscopic measurement image file (which is the image file Ref in this case) in Step S142.

Using these read one-pixel values, the CPU 51 computes the PRI=(R570−R531)/(R570+R531) and calculates the PRI value for each one pixel in Step S143.

The CPU 51 confirms whether or not the process is finished for all the pixels in the spectroscopic measurement image file to be processed in Step S144. If the process is not finished for all the pixels, the CPU 51 returns to Step S141 and performs a similar process on the next pixel.

By repeating this process, the CPU 51 calculates the PRI values for all the pixels in the spectroscopic measurement image file. In other words, at timing at which the CPU 51 determines that computation of all the pixels is finished for the image file Ref in Step S144, the CPU 51 has been able to generate the vegetation index image file Ref_P containing the PRI values as all the pixel values. Thus, the CPU 51 ends the process of FIG. 6 for one spectroscopic measurement image file (for example, the image file Ref).

Upon performing the process described above as Step S105 of FIG. 5, the CPU 51 writes the generated vegetation index image file Ref_P to the vegetation index buffer 23 in Step S105.

The CPU 51 confirms whether or not the currently generated vegetation index image file corresponds to the reference district Aref (whether the currently generated vegetation index image file is "Ref_P") in Step S106.

In other words, the CPU 51 compares the information associated with the irrigation division obtained as the division information PI with the tag information TG, and confirm whether or not the vegetation index image file Ref_P has been generated.

In this case, the CPU 51 can determine that the currently generated vegetation index image file is the vegetation index image file Ref_P corresponding to the reference district Aref by comparing, for example, the information associated with the irrigation division with the position information within the tag information TG added to the image file Ref.

In a case of determining that the vegetation index image file Ref_P corresponding to the reference district Aref has been generated, the CPU 51 calculates the reference value Vref in Step S107. In other words, the CPU 51 reads the vegetation index image file Ref_P from the vegetation index buffer 23.

It is noted that the vegetation index buffer 23 may store the vegetation index image file Ref_P at least until the CPU 51 reads the vegetation index image file Ref_P in Step S107.

The CPU 51 then calculates the reference value Vref by the scheme described above such as obtaining the average value of all the pixels in the read vegetation index image file Ref_P. Subsequently, the CPU 51 goes to Step S108.

The CPU 51 determines whether or not computation of the vegetation indexes is finished for all the spectroscopic measurement image files to be processed in Step S108. If the computation is not finished for all the spectroscopic measurement image files, the CPU 51 returns to Step S102 and performs the process for the other spectroscopic measurement image file.

For example, the CPU 51 next performs the process in Steps S102 to S106 for the image file M1. Therefore, the CPU 51 reads the image file M1 in Step S102, reads the tag information TG in Step S103, and computes the vegetation index in Step S104. In other words, the CPU 51 performs the process of FIG. 6 with the image file M1 set as an object. The CPU 51 thereby generates the vegetation index image file M1_P corresponding to the district to be measured A1.

The CPU 51 writes the vegetation index image file M1_P to the vegetation index buffer 23 in Step S105 of FIG. 5.

In this case, the CPU 51 determines that the currently generated vegetation index image file does not correspond to the reference district Aref, in Step S106; thus, the CPU 51 goes to Step S108 without via Step S107 and confirms whether a remaining spectroscopic measurement image file is present.

The CPU 51 performs a similar process for the image file M2 and the following to generate the vegetation index image files.

When the CPU 51 is finished with computation of the vegetation indexes for all the spectroscopic measurement image files, the CPU 51 goes to Step S109. Here, the CPU 51 performs a process for successively generating the difference image files M1_DP, M2_DP, and the like for the vegetation index image files M1_P, M2_P, and the like of the districts to be measured A1, A2, and the like.

The CPU 51 reads, for example, the vegetation index image file M1_P from the vegetation index buffer 23 in Step S109. The CPU 51 then subtracts the reference value Vref from the value of the vegetation index per pixel in the vegetation index image file M1_P in Step S110. The CPU 51 thereby generates the difference image file M1_DP containing the difference values as all the pixels.

The CPU 51 writes the difference image file M1_DP to the output buffer 27 in Step S111.

The CPU 51 confirms whether or not the process on the vegetation index image files is finished for all the districts to be measured A1, A2, and the like as objects in Step S112, and returns to Step S109 if the process is not finished for all the districts to be measured A1, A2, and the like.

The CPU 51 then reads the other vegetation index image file M2_P from the vegetation index buffer 23 in Step S109, and subtracts the reference value Vref from the value of the vegetation index per pixel in the vegetation index image file M2_P in Step S110. The CPU 51 thereby generates the difference image file M2_DP containing the difference values as all the pixels. The CPU 51 writes the difference image file M2_DP to the output buffer 27 in Step S111.

Upon determining in Step S112 that the process on the vegetation index image files is finished for all the districts to be measured A1, A2, and the like that are objects to be measured this time, the CPU 51 goes to Step S113 to output the difference image files M1_DP, M2_DP, and the like. For example, the CPU 51 outputs the difference image files M1_DP, M2_DP, and the like as images, or generates output data on the basis of the difference image files M1_DP, M2_DP and the like and outputs the generated output data Dout.

The stress information generated for the districts to be measured A1, A2, and the like is thereby output.

Figure 7:
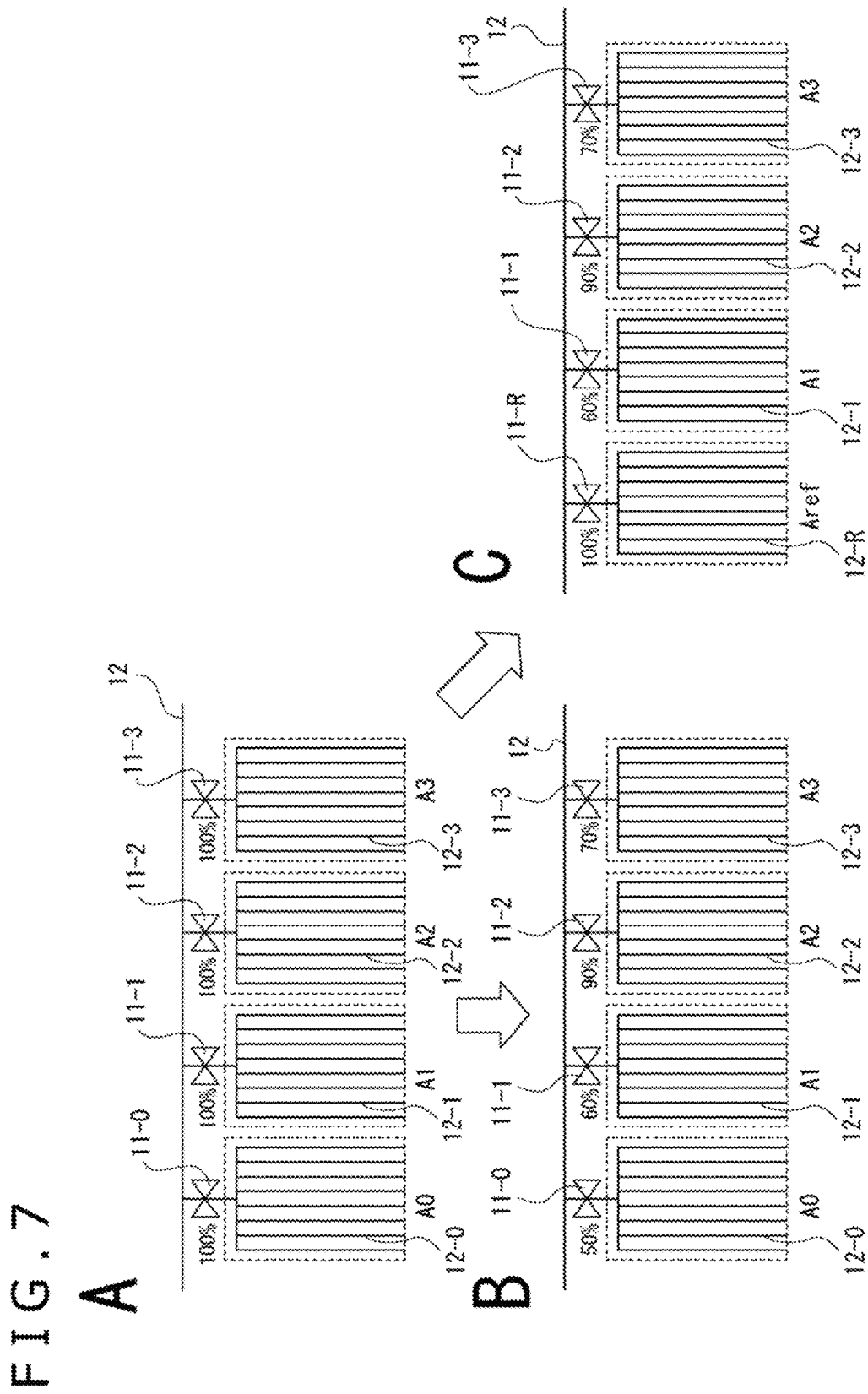
FIG. 7 is an explanatory diagram in a case of providing a reference district in an irrigation control unit according to the embodiment.

An irrigation control unit of the farm field according to the first embodiment will now be described with reference to FIG. 7. FIG. 7 depict a case of creating the reference district Aref generally in irrigation control units (1 ha (10,000 m$^2$)).

FIG. 7A depicts districts A0, A1, A2, and A3 in the farm field. In each district, an irrigation channel 12-0, 12-1, 12-2, or 12-3 is laid and quantity of irrigation water of the irrigation channel 12-0, 12-1, 12-2, or 12-3 can be regulated by an irrigation setting valve 11-0, 11-1, 11-2, or 11-3, respectively.

FIG. 7B depicts a case of setting open rates of the irrigation setting valves 11-0, 11-1, 11-2, and 11-3 to 50%, 60%, 90%, and 70%, respectively as provisional irrigation setting adjusted per location, per weather, or per nurturing stage in such a farm field. However, a water stress is likely to occur in each of the districts A0, A1, A2, and A3 if this setting is not appropriate; thus, obtaining water stress information associated with each district makes it possible to determine an appropriate quantity of irrigation water.

In this case, however, it is difficult to make correct determination since no reference is present. For example, even if a result indicating that a water stress is low is obtained as the stress information associated with the district A2 with the quantity of irrigation water of 90%, it is impossible to determine whether the result is optimum.

It is noted that 100% means herein is a value by an existing irrigation scheme which is either a fixed value that is not adjusted to the location, the weather, or the nurturing stage or a set value that is not sufficiently and individually optimized on those conditions. For example, 100% means that a uniform and sufficient irrigation value is used even in different locations such as A0, A1, A2, and A3. In general, if only the locations are taken into account, a necessary quantity of irrigation varies among the locations due to differences in a drainage performance of the location and components of the soil thereof.

To address the problem, according to the embodiment, the water stress-free reference district Aref is provided and the stress information is generated as the difference information between the vegetation index of the reference district Aref and the vegetation index of each of the districts to be measured.

Owing to this, the district A0, for example, is set as the reference district Aref and the quantity of irrigation water in the district A0 is set to 100% as depicted in FIG. 7C. The other districts A1, A2, and A3 are set to the districts to be measured A1, A2, and A3, and suitable quantities of irrigation water in the districts to be measured A1, A2, and A3 are set, respectively.

Generating the water stress information as described above upon such setting makes it possible to clearly determine whether the quantity of irrigation water is appropriate in a case in which the quantity of irrigation water is to be reduced.

For example, in a case in which conspicuous differences cannot be observed as the difference image files M2_DP and M3_DP corresponding to the districts to be measured A2 and A3 (that is, the districts to be measured A2 and A3 do not greatly differ from the reference district Aref), it is clearly understood that these districts to be measured are irrigated sufficiently or susceptible to further reduction in the quantity of irrigation. In a case in which a conspicuous difference is observed as the difference image file M1_DP for the district to be measured A1, it is clearly understood that the quantity of irrigation is excessively reduced in the district to be measured A1.

2. Second Embodiment

A second embodiment will be described with reference to FIG. 8.

It is noted that in the description of subsequent embodiments, similar constituent sites to those in the embodiment already described are denoted by the same reference characters and repetitive description thereof will be omitted.

The second embodiment is an example in which the reference district Aref is provided as a district adjacent to each district to be measured A ("A" is assumed as a generic notation of A1, A2, and the like) per district to be measured A.

Figure 8:
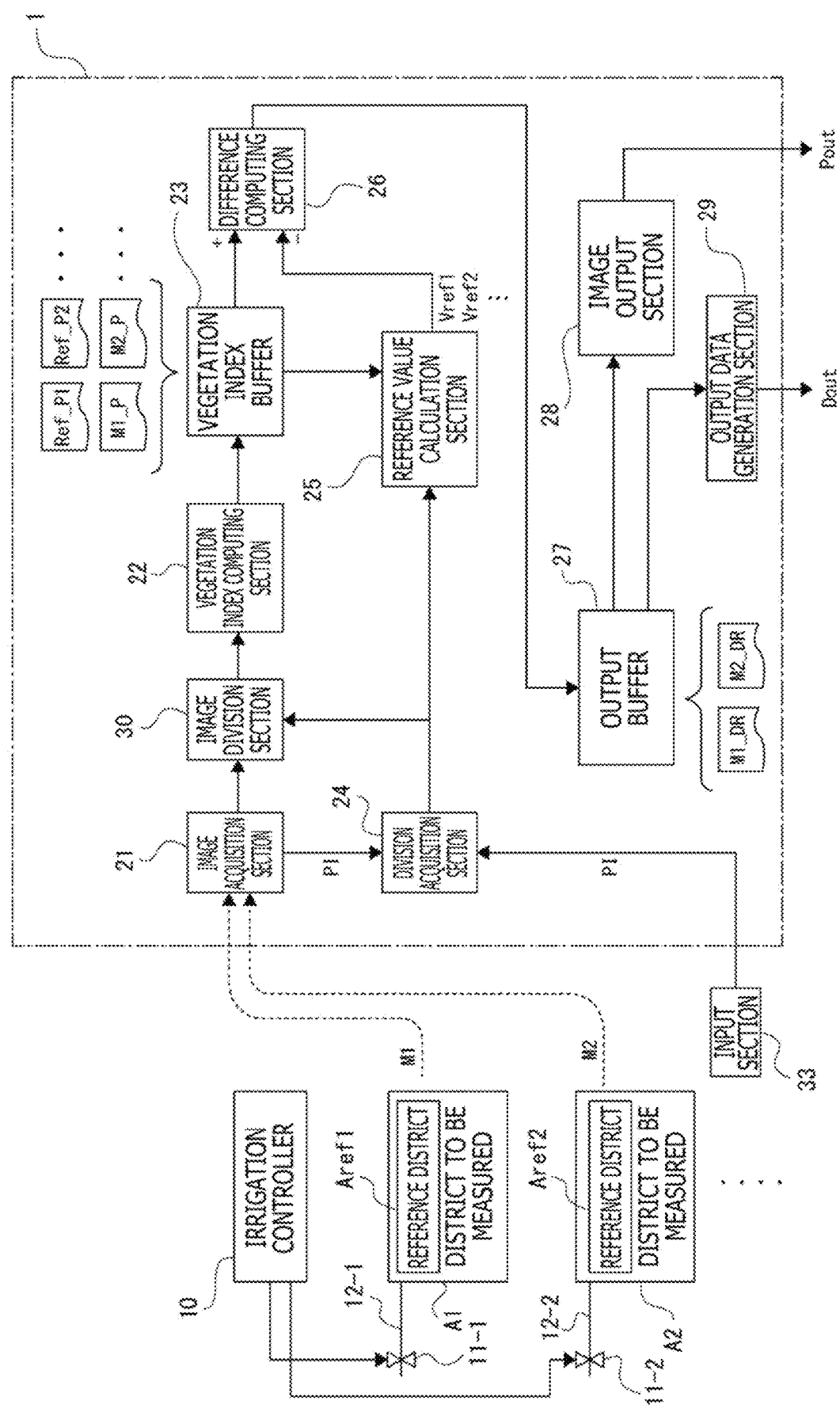
FIG. 8 is an explanatory diagram of a system configuration according to a second embodiment.

For example, as depicted in FIG. 8, a reference district Aref1 is provided within the district to be measured A1 and a reference district Aref2 is provided within the district to be measured A2. (In the case of this second embodiment, it is assumed that "Aref" is a generic notation of Aref1, Aref2, and the like.)

Owing to this, the image files M1, M2, and the like as the captured spectroscopic measurement images each contain a mixture of images of the district to be measured A (A1, A2, or the like) and images of the reference district Aref (Aref1, Aref2, or the like).

It is noted that this second embodiment is an example in which the images of the district to be measured A and the reference district Aref are captured together. The reference district Aref is not limited to the district surrounded by the district to be measured A and may be a district held between the districts to be measured A or a district adjacent to and side by side with the district to be measured A. In other words, the reference district Aref may be provided as a district that is not apart from the corresponding district to be measured A as a section in the farm field.

This FIG. 8 depicts an example in which input information from the input section 33 is input to the division acquisition section 24 in the information generation apparatus 1 as the division information PI.

The input section 33 is, for example, a keyboard, a mouse, and a remote controller corresponding to the input section 57 of FIG. 4, or a portable terminal apparatus such as a smart phone which is an apparatus through which a staffer can input information to the information generation apparatus 1.

For example, information as to how the reference district Aref is disposed relatively to each district to be measured A is input as the division information PI.

Upon forming the reference district Aref in the farm field, the staffer may input information (information associated with a position and a range in the farm field) in response to the formed reference district Aref.

Each of the image files M1, M2, and the like contains a mixture of the images of the district to be measured A and the reference district Aref. This is because the district to be measured A1 and the reference district Aref1, for example, are imaged simultaneously.

Owing to this, it is necessary to divide an image region as the district to be measured A from an image region as the reference district Aref for each of the image files M1, M2, and the like.

The information generation apparatus 1 is thus provided with a function as an image division section 30.

The image division section 30 performs a division process on the basis of the division information PI acquired by the division acquisition section 24. For example, the image division section 30 divides the image region of the district to be measured A1 from the image region of the reference district Aref1 in the image file M1 as the spectroscopic measurement images.

The vegetation index computing section 22 computes PRI values on the basis of the divided images and generates vegetation index image files Ref_P1 and M1_P.

In this case, since the reference district Aref is provided per district to be measured A, the vegetation index image files Ref_P1 and M1_P are generated from the image file M1 and the vegetation index image files Ref P2 and M2_P are generated from the image file M2.

The reference value calculation section 25 calculates the reference value Vref per district to be measured A. In other words, the reference value calculation section 25 generates a reference value Vref1 used for the vegetation index image file M1_P using the vegetation index image file Ref_P1, and generates a reference value Vref2 used for the vegetation index image file M2_P using the vegetation index image file Ref P2.

Figure 9:
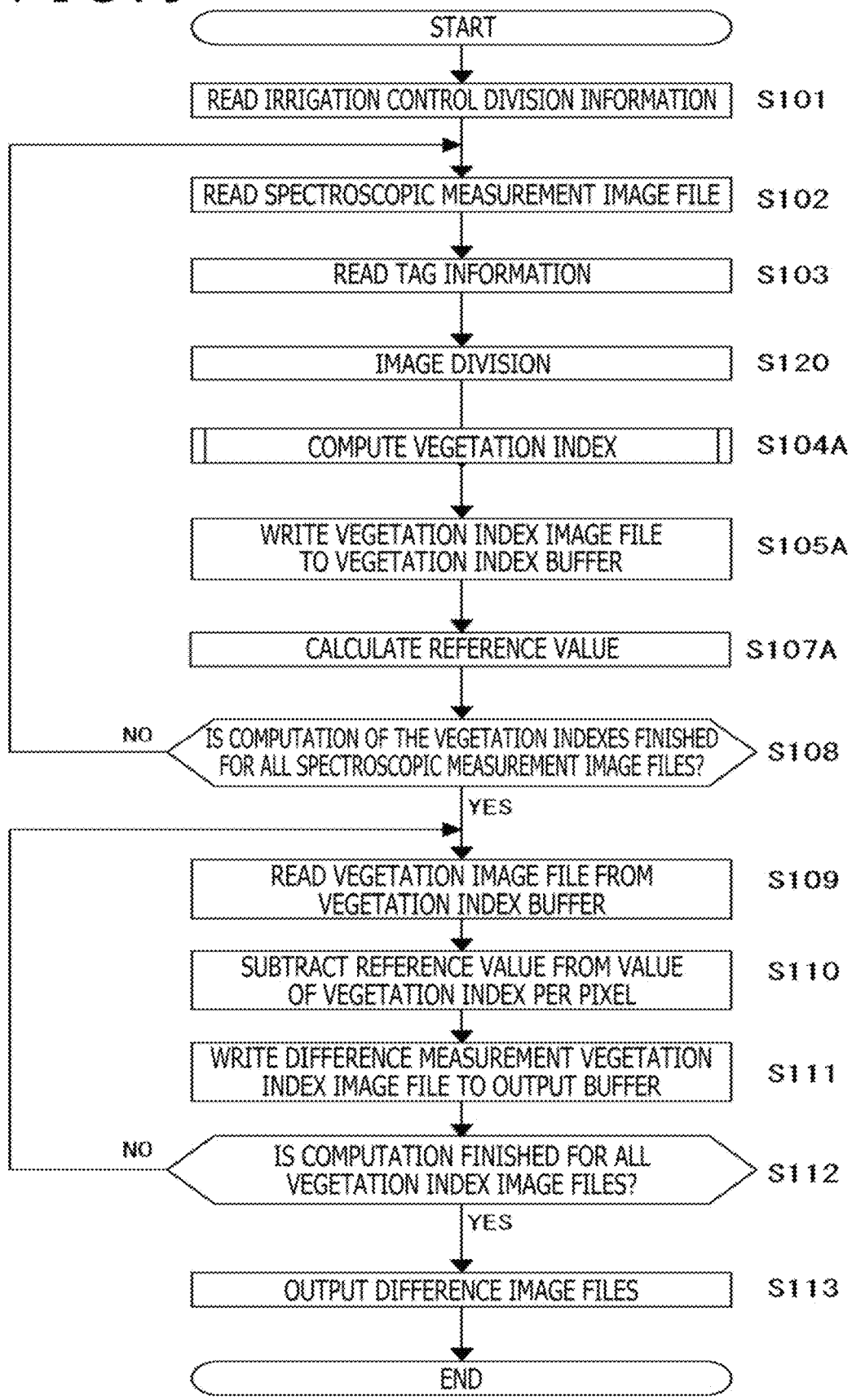
FIG. 9 is a flowchart of a computing process for a vegetation index according to the second embodiment.

FIG. 9 depicts an example of a stress information generation process performed by the computer apparatus 100 (CPU 51) serving as such an information generation apparatus 1. This FIG. 9 depicts basically similar processes to those described with reference to FIGS. 5 and 6 (and in FIG. 9, the same Step numbers are added to the same processes as those in FIG. 5).

It is to be noted that an image division process S120 for dividing the images of the reference district Aref from the images of the district to be measured A is added between Step S103 and Step S104 of FIG. 5 (Step S104A of FIG. 9) since the image files M1, M2, and the like contains the images of the reference district Aref as described above.

For example, the CPU 51 determines what pixel region is the image region of the reference value Vref in the spectroscopic measurement images in the image file M1 using the division information PI (including the tag information TG), and determines the pixel region as the images of the reference district Aref1 and the other region as the images of the district to be measured A1 in Step S120.

Furthermore, the CPU 51 performs the process of FIG. 6 using the divided images of the reference district Aref1 to calculate the PRI, and generates the vegetation index image file Ref_P1 in Step S104A. Furthermore, the CPU 51 similarly performs the process of FIG. 6 using the images of the district to be measured A1 to calculate the PRI, and generates the vegetation index image file M1_P.

The CPU 51 writes these vegetation index image files Ref_P1 and M1_P to the vegetation index buffer 23 in Step S105A.

The CPU 51 then goes to Step S107A to calculate a reference value Vref1 using the vegetation index image file Ref_P1.

Subsequently, the CPU 51 returns to Step S102 from Step S108 if the other image file is not processed yet. For example, the CPU 51 performs a similar process for the image file M2.

In the case of the second embodiment as described above, the reference districts Aref1, Aref2, and the like are provided to be adjacent to the districts to be measured A1, A2, and the like; thus, it is possible to simultaneously obtain the images of the district to be measured A and those of the reference district Aref and to set environmental conditions (for example, the sunshine and the temperature) other than the specific environmental stress (for example, the water stress) identical. This is effective particularly in a case in which a farm land is vast. In an actual farm operation, this scheme is valuable.

Figure 10:
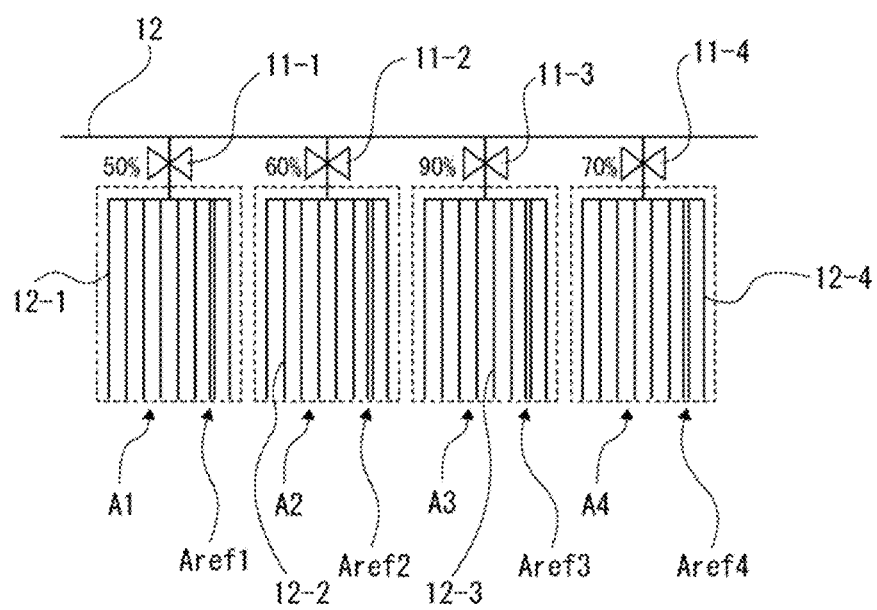
FIG. 10 is an explanatory diagram in a case of providing a reference district within a district to be measured as an irrigation control unit according to the embodiment.

Here, FIG. 10 depicts an example of a method of forming the reference district Aref in the case in which the water stress is assumed as the specific environmental stress.

FIG. 10 depicts districts to be measured A1, A2, A3, and A4. In each of the districts to be measured A, an irrigation channel 12-1, 12-2, 12-3, or 12-4 by an irrigation tube, for example, is arranged.

While the irrigation tubes are normally buried at intervals of one ridge (50 cm to 1 m), two irrigation tubes are buried only partially. These partial portions correspond to the reference districts Aref1, Aref2, Aref3, and Aref4.

While the two irrigation tubes are buried in each of the reference districts Aref, an irrigation tube having large-diameter holes or having holes formed at short intervals may be buried therein.

This makes it possible to realize districts that can be partially irrigated sufficiently even if a set quantity of irrigation of the entire farm field is reduced.

It is noted that open rates of the irrigation setting valves 11-1, 11-2, 11-3, and 11-4 are set to 50%, 60%, 90%, and 70% in this example.

3. Third Embodiment

Figure 11:
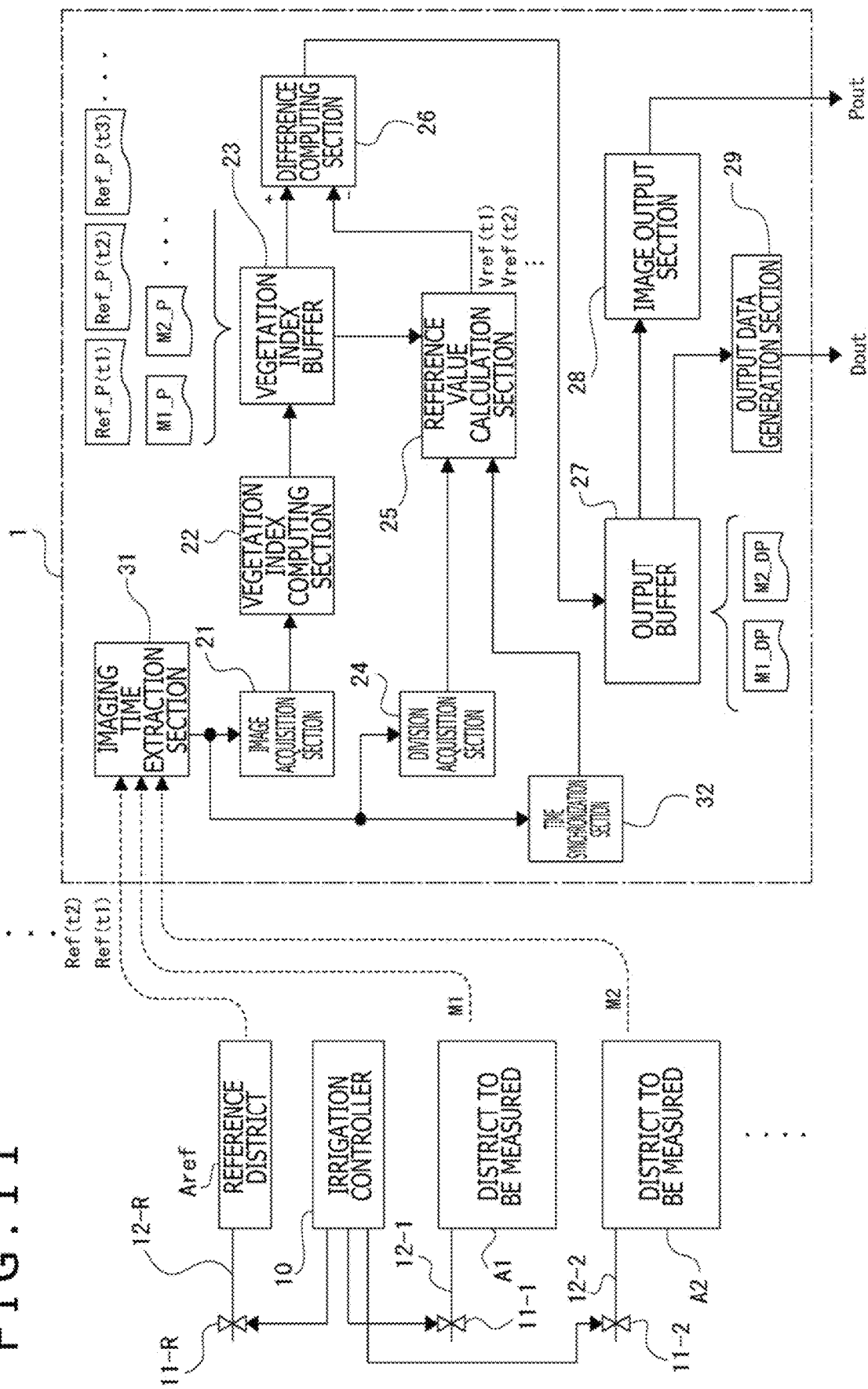
FIG. 11 is an explanatory diagram of a system configuration according to a third embodiment.

An example of a configuration of a third embodiment will be described with reference to FIG. 11.

This embodiment is an example of a case of providing the reference district Aref apart from the districts to be measured A1, A2, and the like similarly to the first embodiment and of imaging the reference district Aref and generating the vegetation index image file thereof separately as needed from imaging the districts to be measured A1, A2, and the like and generating the vegetation index image files thereof.

For example, a fixed point camera is provided for the reference district Aref to image the reference district Aref at intervals of predetermined time. Needless to say, the air vehicle 200 may be caused to fly in the air at intervals of predetermined time to image the reference district Aref with the imaging apparatus 250.

In addition, the vegetation index image file Ref_P is generated whenever the air vehicle 200 flies in the air. In other words, vegetation index image files Ref_P(t1), Ref_P(t2), Ref_P(t3), and the like of the generated reference district Aref are generated at respective time.

The information generation apparatus 1 is provided with functions as an imaging time extraction section 31 and a time synchronization section 32.

The imaging time extraction section 31 extracts imaging time information for the image files Ref, M1, M2, and the like. The imaging time information is input to the division acquisition section 24 as the division information PI. The imaging time information is also supplied to the time synchronization section 32.

The time synchronization section 32 supplies the imaging time information to the reference value calculation section 25 for calculating each reference value Vref.

Figure 12:
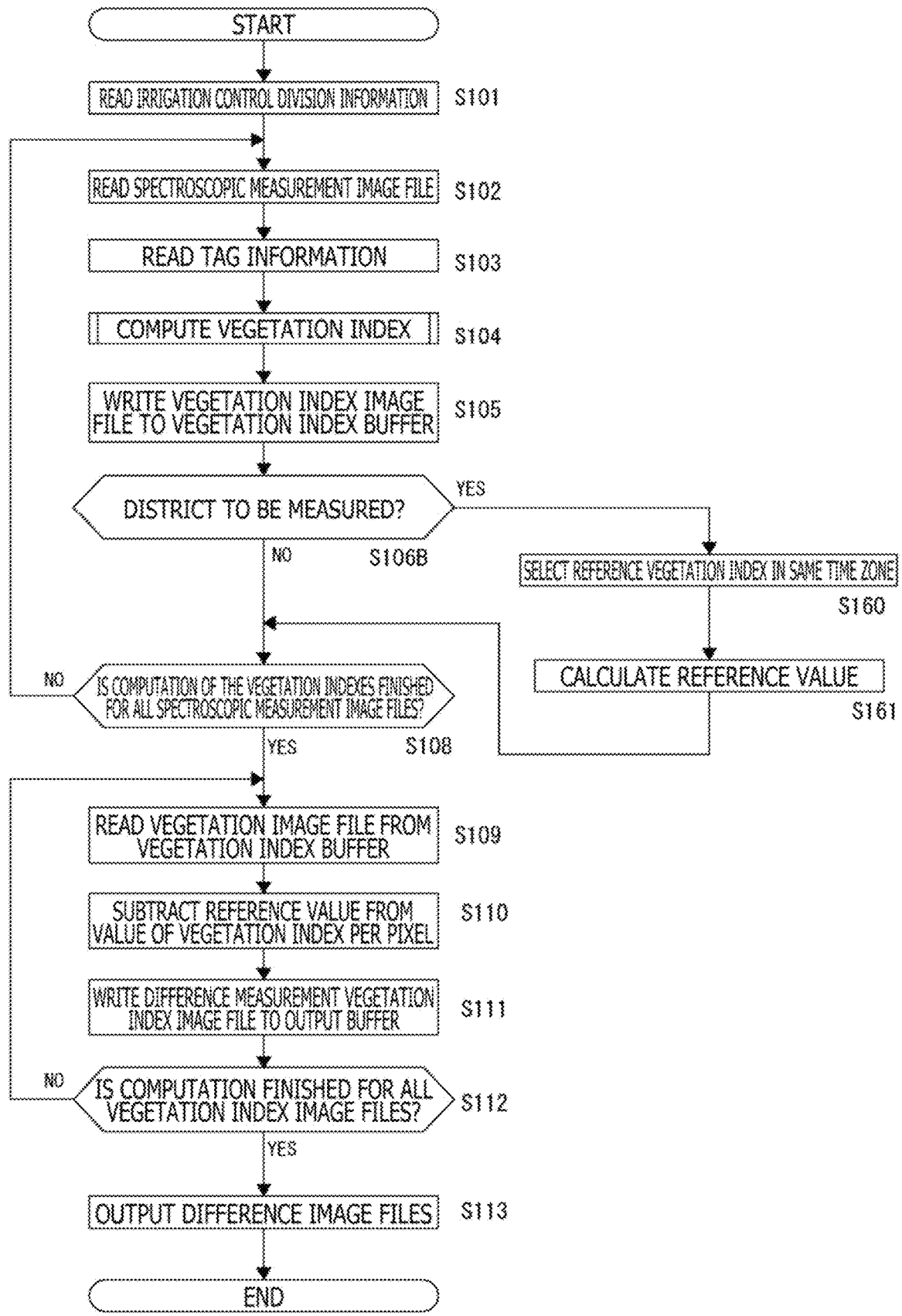
FIG. 12 is a flowchart of a computing process for a vegetation index according to the third embodiment.

FIG. 12 depicts a stress information generation process performed by the computer apparatus 100 (CPU 51) serving as such an information generation apparatus 1. Processes are basically similar to those described with reference to FIGS. 5 and 6 (and in FIG. 12, same Step numbers are added to the substantially similar processes as those in FIG. 5). However, a process for synchronizing imaging time is added as described below since the image files Ref and the image files M1, M2, and the like are not consecutively input.

The image files Ref of the reference district Aref are provided from the imaging apparatus sequentially. FIG. 11 depicts the image files Ref at different timing as image files Ref(t1), Ref(t2), and the like.

The CPU 51 sequentially performs processes in Steps S101 to S105 of FIG. 12 for these image files Ref(t1), Ref(t2), and the like, and generate the vegetation index image files Ref_P(t1), Ref_P(t2), and the like. It is noted, however, it is unnecessary to calculate the reference values Vref at this stage.

The CPU 51 performs the processes of FIG. 12 with the image files M1, M2, and the like of the districts to be measured A1, A2, and the like assumed as objects. In this case, the CPU 51 performs the processes in Steps S101 to S105 of FIG. 12 with the image files M1, M2, and the like successively assumed as objects to be processed, similarly to FIG. 5.

The CPU 51 performs the processes in Steps S101 to S105 for, for example, the image file M1 and generates the vegetation index image file M1_P.

At this time, by determining in Step S106B that the currently generated vegetation index image file is the images of the district to be measured A1, the CPU 51 goes to a process in Step S160, and selects the vegetation index image file Ref_P for the image file Ref of the reference district Aref captured in the same time zone as that of the image file M1. In other words, this is a process for synchronization using the imaging time information extracted from the image file (Ref, M1, M2, or the like).

By this synchronization process, the CPU 51 determines, for the vegetation index image file M1_P, for example, that the vegetation index image file Ref_P(t1) corresponds to the vegetation index image file in the same time zone as that of the vegetation index image file M1_P.

In that case, the CPU 51 generates a reference value Vref(t1) using the vegetation index image file Ref_P(t1) in Step S161. The CPU 51 stores this reference value Vref(t1) as a value corresponding to the vegetation index image file M1_P.

Next, the CPU 51 performs the processes in Steps S101 to S105 for, for example, the image file M2 and generates the vegetation index image file M2_P.

At this time, by determining in Step S106B that the currently generated vegetation index image file is the images of the district to be measured A2, the CPU 51 goes to the process in Step S160, and selects the vegetation index image file Ref_P for the image file Ref of the reference district Aref captured in the same time zone as that of the image file M2. In addition, the CPU 51 determines, for the vegetation index image file M2_P, that the vegetation index image file Ref_P(t2) corresponds to the vegetation index image file in the same time zone as that of the vegetation index image file M2_P.

In that case, the CPU 51 generates a reference value Vref(t2) using the vegetation index image file Ref_P(t2) in Step S161. The CPU 51 stores this reference value Vref(t2) as a value corresponding to the vegetation index image file M2_P.

Processes in Steps S109 to S113 are similar to those in FIG. 5. It is noted, however, that the reference values Vref(t1), Vref(t2), and the like corresponding to the vegetation index image files M1_P, M2_P, and the like are used as the reference values Vref in Step S110.

This third embodiment is suited for a case of measuring vegetation in, for example, a vast farm land.

If it is assumed, for example, that it takes ten minutes for the air vehicle 200 to fly in the air to image one district to be measured A and the number of districts to be measured A is 20, a difference of 200 minutes is generated between imaging time of the district to be measured A1 and that of the district to be measured A20.

If it takes long time to measure the districts to be measured A in this way, the districts to be measured A greatly different in measurement time from the reference district Aref are generated. In this case, environmental conditions such as a sunshine condition and the temperature change, with the result that conditions other than the environmental stress to be calculated change between the districts to be measured A and the reference district Aref.

To address the problem, the reference district Aref is imaged sequentially. By doing so, the images of the reference district Aref captured substantially at the same time as that of each of the districts to be measured A1 to A20 are present, and those images make it possible to obtain the reference values Vref in the corresponding time zones.

It is, therefore, possible to obtain the difference image files M1_DP, M2_DP, and the like by the reference values Vref in the case of setting generally identical the environmental conditions other than the specific environmental stress.

While the reference value Vref is calculated in Step S161 at a time of generating the vegetation index image file of each district to be measured A in the example of the processes of FIG. 12, the reference values Vref(t1), Vref(t2), and the like may be calculated and stored whenever the vegetation index image files Ref_P(t1), Ref_P(t2), and the like of the reference district Aref are generated. In that case, the CPU 51 may select the corresponding reference value Vref using the imaging time information at a time of Step S110.

The time zone used in determination may be set as a time width with which the other environmental conditions can be regarded as substantially the same. The time zone may be determined depending on a location, installation, a climate, and the like of the farm land.

4. Fourth Embodiment

Figure 13:
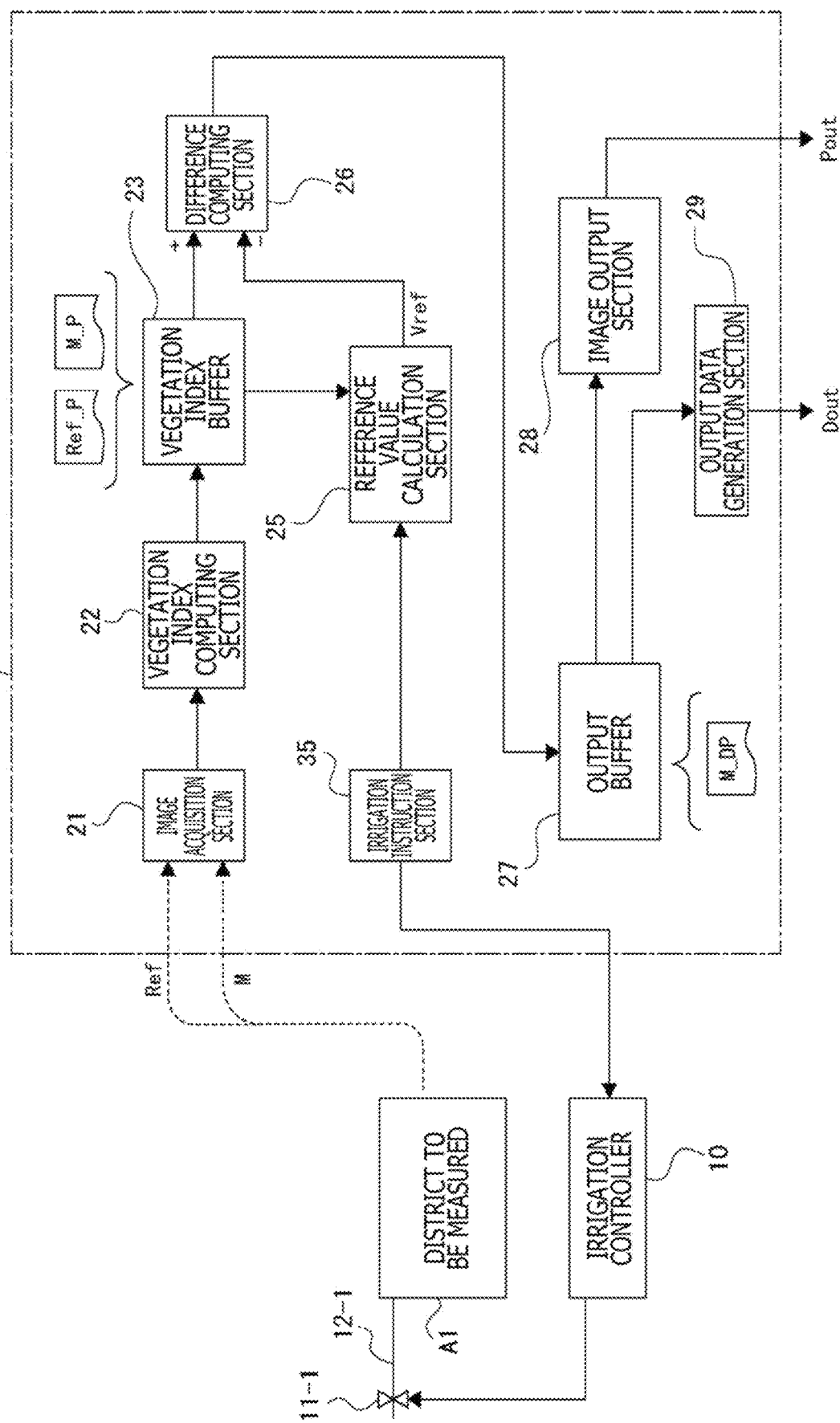
FIG. 13 is an explanatory diagram of a system configuration according to a fourth embodiment.

FIG. 13 depicts an example of a configuration of a fourth embodiment.

In this embodiment, an irrigation instruction section 35 is provided in the information generation apparatus 1. Furthermore, the reference district Aref is not particularly provided in the farm field.

The irrigation instruction section 35 instructs the irrigation controller 10 in the quantity of irrigation. The irrigation controller 10 drives and controls the irrigation setting valve 11-1 for the district to be measured A1 to control the quantity of irrigation water in the district to be measured A1.

For example, the irrigation instruction section 35 can instruct the irrigation controller 10 in 100% irrigation, 90% irrigation, 80% irrigation, or the like as the quantity of irrigation water. The irrigation controller 10 drives and controls the irrigation setting valve 11-1 in response to this instruction.

Furthermore, the irrigation instruction section 35 conveys quantity-of-irrigation-water instruction information at each time to the reference value calculation section 25.

In a case of this configuration, captured images at a time of setting the quantity of irrigation water to 100% are used as the image file Ref and captured images at a time of reducing the quantity of irrigation water (setting the quantity of irrigation water to, for example, 70%) are used as an image file M of the district to be measured A1.

A stress information generation process performed by the computer apparatus 100 (CPU 51) serving as the information generation apparatus 1 is similar to that in FIGS. 5 and 6.

However, the CPU 51 determines in Step S106 whether the generated vegetation index image file is the vegetation index image file Ref_P as a reference or a vegetation index image file M_P of the district to be measured A1. In a case in which the generated vegetation index image file is the vegetation index image file Ref_P as the reference, the CPU 51 may calculate the reference value Vref in Step S107.

For example, since the time of setting the quantity of irrigation water to 100% is known, the CPU 51 may handle the vegetation index image file generated using the image file at that time as the vegetation index image file Ref_P.

Figure 14:
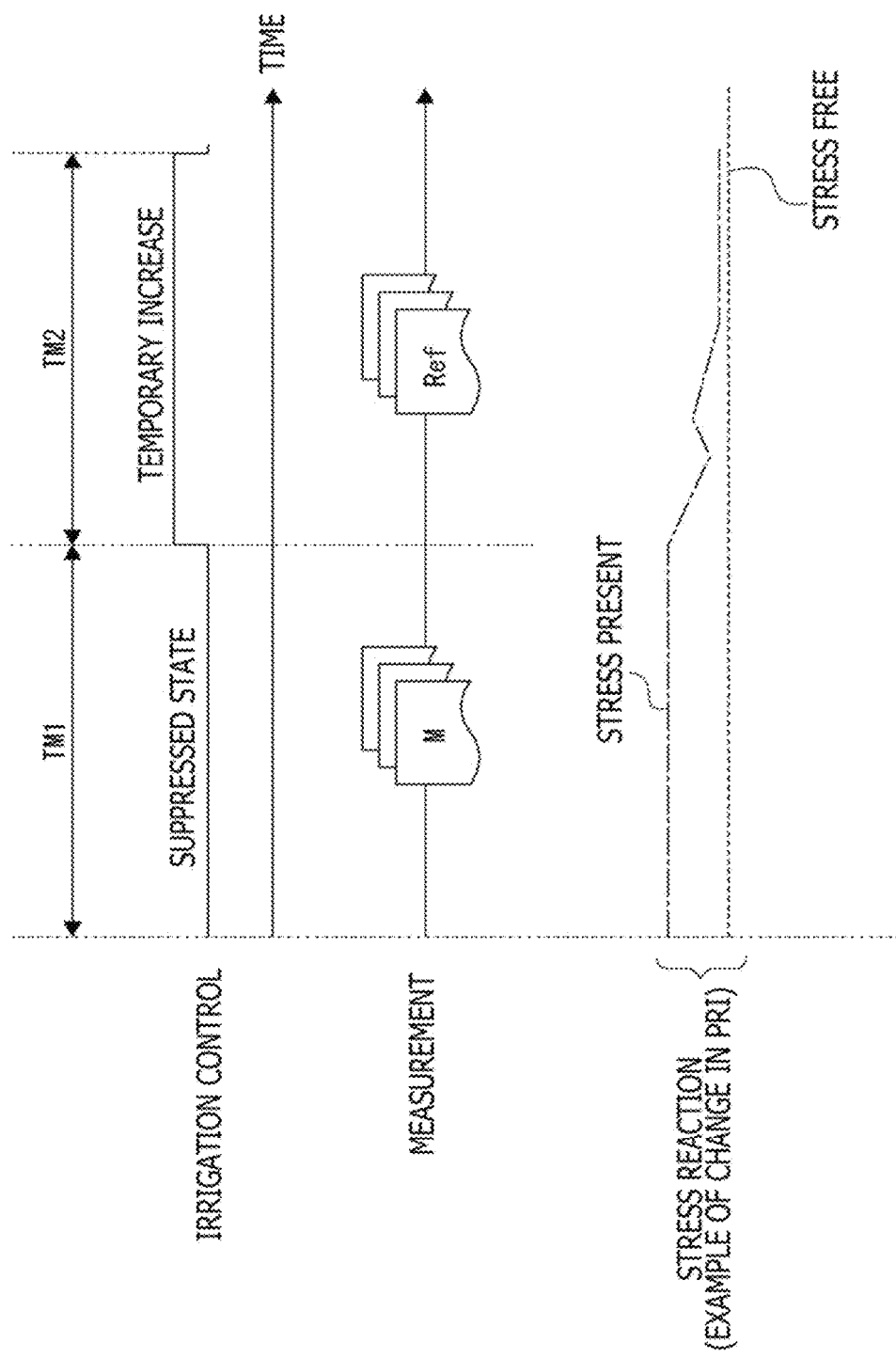
FIG. 14 is an explanatory diagram of stress reaction observation according to the fourth embodiment.

Generation of the vegetation index image files Ref_P and M_P in a case of measurement with the quantity of irrigation water controlled intentionally in this way will be described with reference to FIG. 14.

A time period TM1 is one in which irrigation control is set in a suppressed state (of setting the quantity of irrigation water to, for example, 70%).

From the image file M (spectroscopic measurement images) captured in this time period TM1, a high stress reaction is observed as the PRI values.

A time period TM2 is one in which the irrigation control is in a temporary increase state (of setting the quantity of irrigation water to, for example, 100%).

From the image file Ref (spectroscopic measurement images) captured in this time period TM2, the PRI values fall and a stress-free state is observed.

Therefore, performing difference computation between the reference value Vref obtained from the vegetation index image file Ref_P for this time period TM2 and the vegetation index image file M_P for the time period TM1 using the reference value Vref makes it possible to obtain an appropriate difference image file M_DP with respect to the water stress.

In the fourth embodiment described so far, measurement is made to determine whether the specific environmental stress occurs by whether a change in a measurement value appears by controlling a specific environment. At this time, it is conceivable that the specific environment is controlled stepwise, an environment set value (for example, the temperature or the quantity of irrigation) of stress free is recorded, and environmental stress variable installation (for example, the irrigation setting valve 11-1) is automatically controlled with this recorded value assumed as an optimum environment set value. The environmental stress variable installation means herein an apparatus for changing environmental states (the quantity of water, the temperature, a $CO_2$ concentration, and the like) to affect the environmental stress on the plant either directly or indirectly. The environmental stress variable installation is not limited to the irrigation setting valve exemplarily described and examples of the environmental stress variable installation may include an illumination lamp, a heater, and a $CO_2$ generator.

For example, the optimum environment set value on various environmental conditions (except for a condition for affecting the specific environmental stress) is recorded in advance, and the environmental stress variable installation is controlled while setting an environment set value on the closest condition at timing at which a difference value is positive (indicating that a stress is present) as a target value. Specifically, the irrigation instruction section 35 issues an instruction to the irrigation controller 10 to control the quantity of irrigation water (irrigation setting valve 11-1) of the district to be measured A1. In other words, the environmental stress variable installation is controlled to change the environmental states in such a manner as to reduce the environmental stress on the plant.

That is, automatically controlling the irrigation setting valve 11-1 that regulates the quantity of irrigation and the like on the basis of the information associated with a difference from the reference value Vref makes it possible to exercise desirable irrigation control based on an observation result.

5. Setting of Quantity of Irrigation

Another example of a scheme for setting the quantity of irrigation that can be adopted in each of the embodiments described so far will next be described.

While examples of the scheme for setting the quantity of irrigation in each district have been described previously with reference to FIGS. 7 and 10, FIG. 15 depict another example of the scheme.

FIG. 15A depicts an irrigation tube 120 used as the irrigation channel 12. At timing of purchase of the irrigation tube 120, holes are not particularly formed in the irrigation tube 120. For example, a tractor for use in installing the irrigation tube 120 in the farm field is equipped with a perforation mechanism. In addition, at the time of installing the irrigation tube 120, the irrigation tube 120 is installed while forming holes 120H as depicted in FIG. 15C.

In this case, making intervals of the holes 120H variable or setting different hole diameters makes it possible to make the quantity of irrigation water differ among sections of the irrigation tube 120.

FIG. 15B depicts an example of setting quantities of irrigation water to be different among the sections of the irrigation tube 120 in a range from 80% to 200%.

Figure 16:
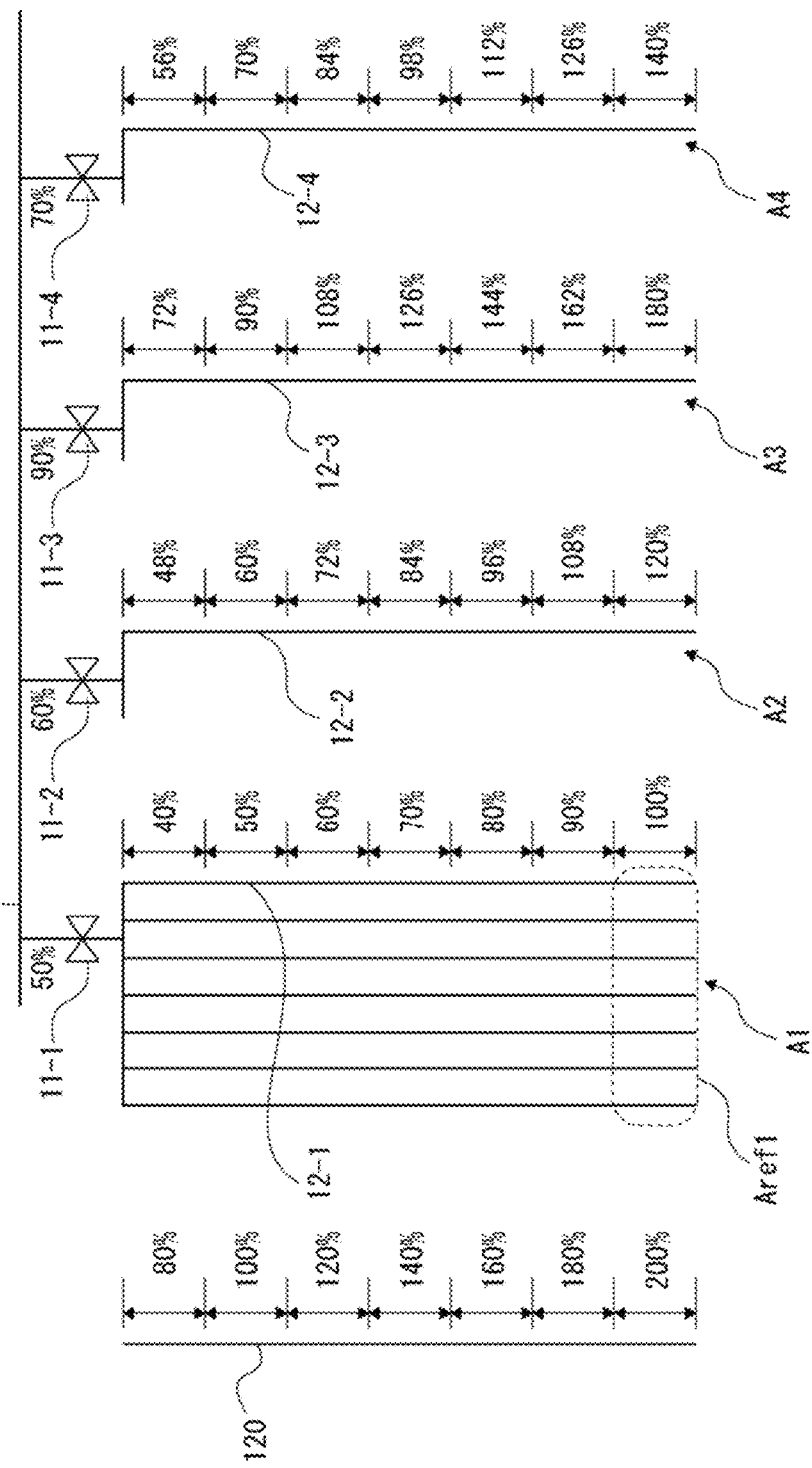
FIG. 16 is an explanatory diagram in a case of changing the quantity of irrigation stepwise in each district to be measured by the irrigation tube according to the embodiments.

FIG. 16B depicts an example of using the irrigation tube 120 set as depicted in FIG. 15B. FIG. 16A depicts the same irrigation tube 120 as that of FIG. 15B.

The irrigation tube 120 of FIG. 16A is used as irrigation channels 12-1, 12-2, 12-3, and 12-4 in districts to be measured A1, A2, A3, and A4 as depicted in FIG. 16B. It is noted that FIG. 16B depicts a state in which a plurality of irrigation tubes 120 is disposed in parallel only in the district to be measured A1 as a whole while the districts to be measured A2, A3, and A4 are omitted and depicted only partially. However, disposition of the irrigation tubes 120 in each district to be measured A is not limited to disposition in parallel and one irrigation tube 120 may be installed in each district to be measured A.

Opens of the irrigation setting valves 11-1, 11-2, 11-3, and 11-4 are set to 50%, 60%, 90%, and 70%, respectively.

This setting makes it possible to minutely set the quantities of irrigation water in the portions of the farm field as depicted in FIG. 16B.

In addition, if each of the districts to be measured with the quantity of irrigation water is assumed as the district to be measured A1, A2, or the like, it is possible to obtain water stress information (difference image files M1_DP, M2_DP, and the like) for various quantities of irrigation water.

In the district to be measured A1, for example, for which the quantity of irrigation is set to 50%, districts with quantities of irrigation of 40% to 90% are present in addition to the reference district Aref1 with the quantity of irrigation of nearly 100%. In a case in which the stress is not measured with the quantity of irrigation up to 50%, it is understood that an optimum irrigation setting is 50%. This facilitates determining what degree of quantity of irrigation water is optimum without repeating cut-and-trial for making measurement while changing the quantity of irrigation water.

6. Detection of Damage in Irrigation Channel

Meanwhile, the information generation apparatus 1 according to the embodiments can detect a damage in the irrigation channel 12 formed by the irrigation tube 120 or the like.

Figure 17:
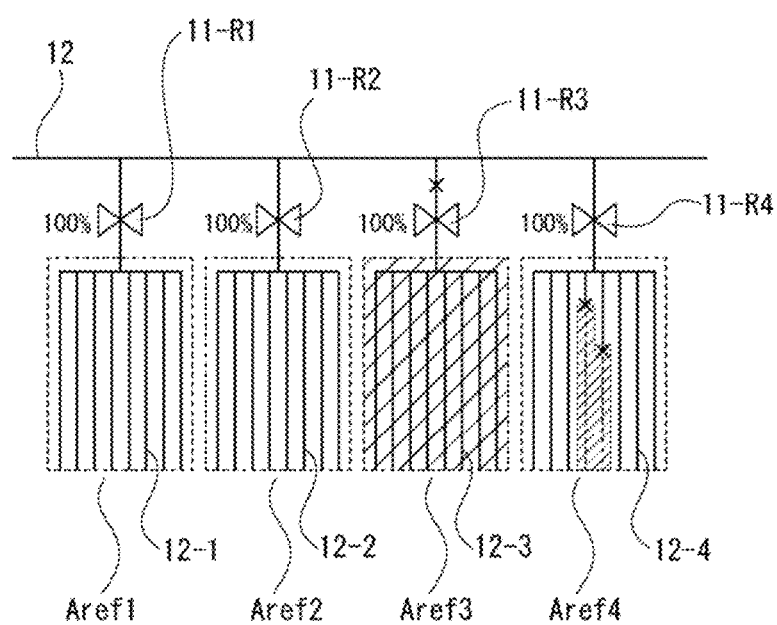
FIG. 17 is an explanatory diagram in a case of detecting a damage in an irrigation channel according to the embodiments.

FIG. 17 depicts, for example, four reference districts Aref1, Aref2, Aref3, and Aref4. Quantity of irrigation water is regulated in each of the reference districts Aref1, Aref2, Aref3, and Aref4 by an irrigation setting valve 11-R1, 11-R2, 11-R3, or 11-R4. Since the districts are all the reference districts Aref, the quantities of irrigation water are all set to 100%.

Vegetation index image files Ref_P are generated from the image files Ref for the four reference districts Aref1, Aref2, Aref3, and Aref4, and reference values Vref are obtained.

Since the reference districts are all in the same water stress state, the respective reference values Vref can be generally equivalent values.

However, it is assumed in the reference district Aref3, for example, that the irrigation channel 12 reaching the irrigation setting valve 11-R3 has a damage and the quantity of irrigation water is 0% in substantially entire regions (shaded portions). It is also assumed in the reference district Aref4 that part of the irrigation channel 12-4 has a damage and a shaded portion is not irrigated appropriately.

In such a case, the reference values Vref obtained for the reference districts Aref3 and Aref4 are greatly different from the reference values Vref obtained for the reference districts Aref1 and Aref2.

As a result, in the case like an example of the reference districts Aref3 and Aref4, it is thereby possible to detect that an appropriate irrigation is not performed due to occurrence of a damage or the like in the irrigation tube.

Therefore, providing, for example, a plurality of reference districts Aref in the first embodiment and comparing the reference values Vref from those reference districts Aref make it possible to determine whether an abnormality occurs in any of the reference districts Aref.

Since the occurrence of an abnormality in any of the reference districts Aref prohibits appropriate measurement of the environmental stress, this abnormality detection scheme is valuable.

Furthermore, it is conceivable that when an abnormality is detected in a certain reference district Aref, the above-mentioned processes are performed using the captured images of the other reference district Aref.

It is thereby possible to make appropriate stress measurement even if part of the reference districts has an abnormality.

The number of reference districts Aref to be installed may be determined in the light of a failure rate of an irrigation system.

Meanwhile, while this example is an example of detection of an abnormality in the reference district Aref, an abnormality can be detected by providing a plurality of districts regardless of the reference district Aref or the district to be measured A, having different irrigation paths, but having the same quantity of irrigation water and comparing measurement results (for example, PRI average values) for the districts.

In a vast farm, for example, it is not easy to locate an abnormality in the irrigation channel 12 due to a damage or the like in the irrigation tube 120. Owing to this, it is suitable as system utilization that an abnormality in the irrigation channel can be detected using processing operations of the information generation apparatus 1.

7. Measurement of Other Environmental Stress

The above embodiments have been described with the case of measuring the water stress as the specific environmental stress taken by way of example; however, needless to say, the technique of the embodiments can be similarly applied to the other environmental stress.

For example, a nitrogen stress can be measured.

Figure 18:
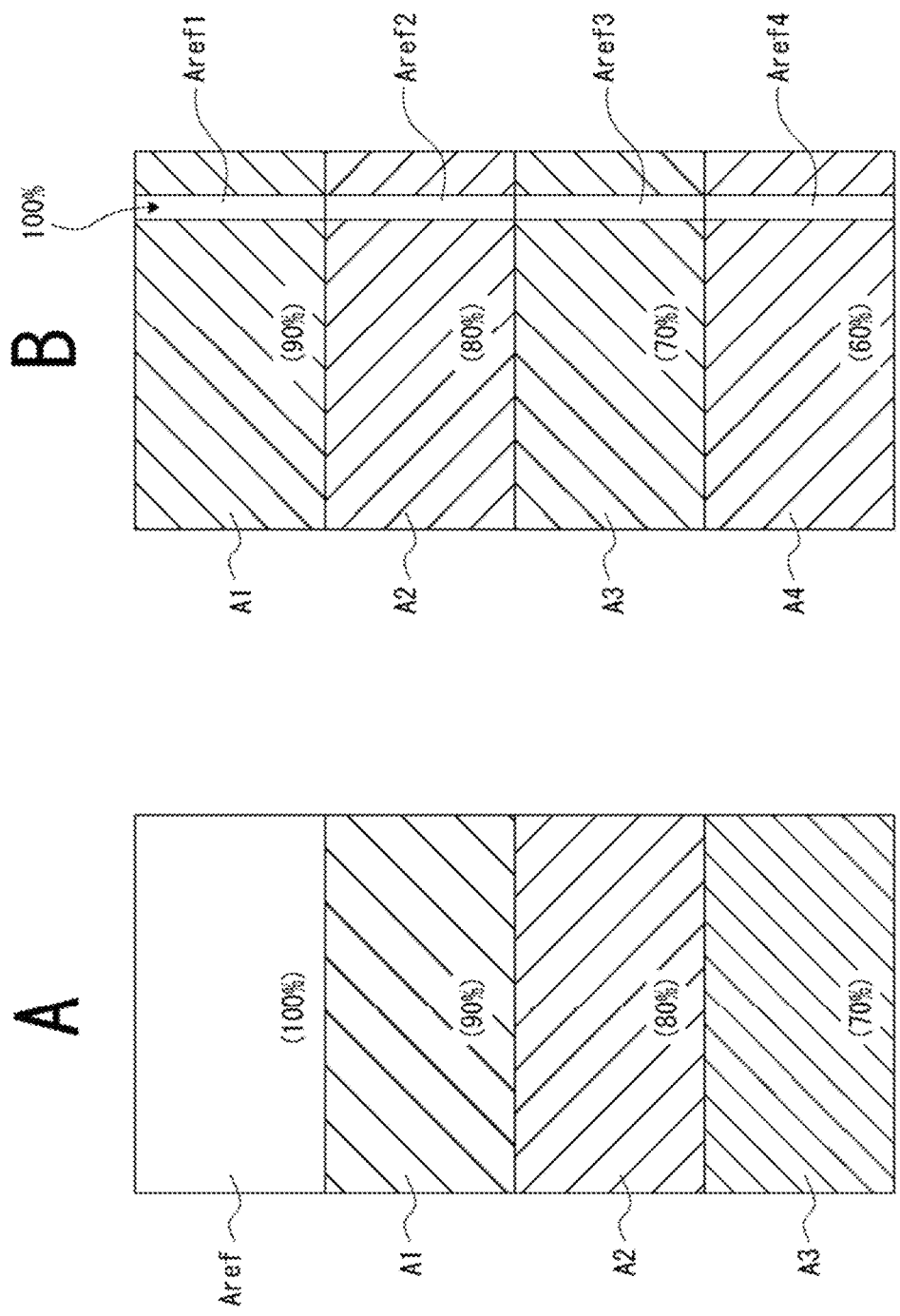
FIG. 18 is an explanatory diagram of fertilization for measurement of a nitrogen stress according to the embodiments.

In the case of providing the reference district Aref as in the first embodiment, divisions are set as depicted in FIG. 18A. An amount of applied fertilizer in the reference district Aref is set to 100%, and those in the districts to be measured A1, A2, and A3 are set to 90%, 80%, and 70%, respectively.

Performing the processes in the first embodiment in such a state makes it possible to obtain the difference image files M1_DP, M2_DP, and M3_DP for determining how much amount of applied fertilizer is appropriate.

In a case of applying the second embodiment to the measurement of the nitrogen stress, divisions are set as depicted in FIG. 18B. For example, amounts of applied fertilizer in the districts to be measured A1, A2, A3, and A4 are set to 90%, 80%, 70%, and 60%, respectively. Reference districts Aref1, Aref2, Aref3, and Aref4 each with an amount of applied fertilizer set to 100% are provided to be adjacent to the respective districts.

Performing the processes in the second embodiment in such a state makes it possible to obtain the difference image files M1_DP, M2_DP, M3_DP, and M4_DP for determining how much amount of applied fertilizer is appropriate.

Needless to say, the vegetation index may not be the index indicating the stress such as the PRI but may be an index indicating a growth result such as an NDVI.

If lines are recognized by visually checking NDVI images, it can be determined that fertilization is inappropriate. This is because a case in which the lines of the reference districts Aref can be visually confirmed is a case in which the reference district Aref and the district to be measured A differ in vegetation state.

It is supposed that types of the environmental stresses on vegetation that can be measured in the embodiments include not only the water stress and the nitrogen stress but also a low-temperature stress, a high-temperature stress, a drying stress, and a stress caused by a shortage of $CO_2$.

8. Conclusion and Modifications

The above embodiments can attain the following effects.

An information generation method by the information generation apparatus 1 according to the embodiments includes: a vegetation information acquisition procedure (S104 of FIG. 5 and FIG. 6) of acquiring vegetation information using a captured image of vegetation; a reference vegetation information acquisition procedure (S107 of FIG. 5; S107A of FIG. 9; S161 of FIG. 12) of obtaining reference vegetation information (reference value Vref) associated with vegetation information in a state of being free of a specific environmental stress; and a difference acquisition procedure (S109, S110, and S111) of acquiring difference information between vegetation information acquired from a captured image of vegetation in a state of being likely to have the specific environmental stress and the reference vegetation information as information associated with the environmental stress.

Obtaining the reference vegetation information (reference value Vref) with the state of being free of the specific environmental stress, which is, for example, a water stress, assumed as a reference and obtaining a difference between the vegetation information acquired from a captured image of a district in which the specific environmental stress is likely to occur and the reference vegetation information make it possible to acquire the information associated with the specific environmental stress highly accurately and relatively easily.

It is possible to grasp the specific environmental stress in an environment such as an outdoor farm field where a plurality of environmental stresses is likely to occur simultaneously, and to optimize discrimination of causes of the environmental stresses and crop management using a result of discrimination.

Furthermore, in a case in which a reduction in the quantity of irrigation water, a reduction in fertilizers, or the like is desired, it is thereby possible to precisely grasp a range in which the environmental stresses do not affect vegetation by executing such a reduction. Therefore, it is possible to provide quite useful information for the appropriate reduction in the quantity of irrigation water or the reduction in fertilizers.

While the processes based on the captured images have been described, data is not limited to images. Vegetation information can be also obtained using, for example, imaging signals of vegetation obtained by imaging wavelength range components or the like.

In the first, second, and third embodiments, vegetation information (vegetation index image file Ref_P) associated with the reference district is obtained from a captured image (image file Ref) of the reference district Aref set into the state of being free of the specific environmental stress. Furthermore, vegetation information (vegetation index image file M1_P, M2_P, or the like) associated with the district to be measured from a captured image M1, M2, or the like of the district to be measured A1, A2, or the like set into the state of being likely to have the specific environmental stress is obtained. Moreover, by calculating the reference value Vref using the vegetation information associated with the reference district Aref and performing computation of a difference between the vegetation information associated with the district to be measured and the reference value Vref, difference information (difference image file M1_DP, M2_DP, or the like) is obtained.

For example, part of the farm field is assumed as the reference district Aref. The reference district Aref is assumed, for example, in the state of water stress-free. The other part of the farm field is assumed as the districts to be measured A (A1, A2, or the like), and the districts to be measured A are assumed in a state of having different irrigation conditions.

Dividing the districts in this way makes it possible to form a state in which the specific environmental stress which is, for example, the water stress differs upon making generally similar the other environmental stresses. Furthermore, imaging the reference district Aref and the district to be measured A substantially at the same time makes it possible to accurately acquire information associated with, for example, the water stress (difference image file M1_DP, M2_DP, or the like) from the captured images of the districts.

In the first embodiment, the reference district Aref is provided in a location apart from the district to be measured A.

This can facilitate setting the reference district Aref as a district which is free of the specific environmental stress and setting the district to be measured A as a district which is likely to have the specific environmental stress.

Providing the reference district Aref as a district different in, for example, irrigation installation from the district to be measured A facilitates setting the reference district Aref free of the water stress and the district to be measured A likely to have the water stress by regulating the quantity of irrigation water by each irrigation installation.

In the second embodiment, the example of providing the reference district Aref to be adjacent to each district to be measured A has been mentioned.

For example, the reference district Aref is provided, for example, within the same irrigation control unit as that of the district to be measured A.

This facilitates imaging the reference district Aref and the district to be measured A substantially at the same time. The reference district Aref can be present in the same captured image as that in which the district to be measured A is present.

Particularly in a case of supposing a vast farm, providing the reference district Aref to be apart from the district to be measured A as in the first embodiment often makes it difficult to image the reference district Aref and the district to be measured A in the same time zone. In this case, the reference district Aref and the district to be measured A possibly differ in the other environmental conditions. To image the reference district Aref and the district to be measured A at the same time as much as possible to avoid this difference, it is necessary, for example, to image the districts by a plurality of air vehicles 250 or to provide fixed point cameras in a plurality of locations, resulting in increases in an installation cost and an operational cost.

Adopting the configuration as described in the second embodiment makes it possible to image the reference district Aref and the district to be measured A substantially at the same time without entailing these cost increases. In other words, it is possible to easily acquire images on the environmental conditions different from each other only in the specific environmental stress at a low cost as the images of the reference district Aref and the district to be measured A.

In the third embodiment, the reference vegetation information (reference value Vref) used to perform the computation of the difference between the vegetation information associated with the district to be measured A and the reference vegetation information is calculated by using vegetation information obtained from a captured image of the reference district Aref that is determined to be identical in a time zone to the captured image used for obtaining the vegetation information associated with the district to be measured A.

The district to be measured A and the reference district Aref can be imaged in the same time zone in some cases, and cannot be imaged in the same time zone in other cases, depending on mechanical equipment circumstances such as the number, the type, and the performance of the imaging apparatus and circumstances such as dimensions of the farm. If the district to be measured A and the reference district Aref are imaged in different time zones, changing environmental conditions such as the sunshine condition and the temperature causes a change in the conditions other than the specific environmental stress to be calculated. To address the problem, vegetation information for calculating the reference value Vref is selected using the imaging date information added to the captured image.

It is thereby possible to compare the vegetation information associated with the district to be measured A with the vegetation information (reference value Vref obtained from the vegetation information) associated with the reference district Aref on substantially the same environmental conditions in the same time zone even in a case in which the reference district Aref and the district to be measured A cannot be imaged at the same time. Therefore, the difference information has values precisely expressing the specific environmental stress (for example, water stress) to be measured, thus making it possible to improve measurement reliability.

The same time zone may be set as the time width or the like with which the other environmental conditions are estimated substantially the same.

In the fourth embodiment, vegetation information (vegetation index image file Ref_P) is obtained from a first captured image (image file Ref) indicating the district to be measured A imaged when the district to be measured A is set into the state of being free of the specific environmental stress, and vegetation information (vegetation index image file M_P) is obtained from a second captured image (image file M) indicating the district to be measured A imaged when the district to be measured A is set into the state of being likely to have the specific environmental stress. Furthermore, the reference vegetation information (reference value Vref) is calculated using the vegetation information obtained from the first captured image, and the computation of the difference between the vegetation information (vegetation index image file M_P) obtained from the second captured image and the reference value Vref is performed.

Variably controlling the specific environmental stress which is, for example, the water stress in the same district to be measured A makes it possible to acquire information associated with the specific environmental stress by the difference computation with high accuracy.

Furthermore, in this case, there is no need to prepare the reference district Aref separately from the district to be measured.

Moreover, dynamically controlling a nurturing environment and making measurement while changing the environmental stresses enable measurement related to the specific environmental stress without relying on the environment (for example, without relying on the weather).

While the example of controlling the quantity of irrigation of the irrigation system and changing the soil moisture content to measure the water stress has been described in this fourth embodiment, the following scheme is conceivable as control over the specific environmental stress.

It is conceivable that air conditioning is controlled to change the temperature for measuring, for example, a low-temperature or high-temperature stress.

It is also conceivable that the air conditioning is controlled to change a saturation deficit for measuring a drying stress.

Moreover, it is conceivable that a carbon dioxide generator is controlled to change a $CO_2$ concentration for measuring a stress caused by a shortage of $CO_2$.

In the first to fourth embodiments, the example of generating the image information (difference image file M1_DP or the like) as the difference information has been described. In other words, the image information represents the difference between the vegetation information acquired from the captured image of the vegetation in the state of being likely to have the specific environmental stress and the reference vegetation information (reference value Vref).

Generating such image information that represents a stress state corresponding to each position in the farm field makes it possible to provide information that enables a person (staffer) to easily recognize the stress state in each location.

In the first to fourth embodiments, the example of calculating the average value of the vegetation information in the state of being free of the specific environmental stress in calculating the reference vegetation information (reference value Vref) has been described.

Using the average value in a course of calculation makes it possible to absorb unevenness per individual piece within, for example, the reference district to acquire the appropriate reference value Vref.

The information generation apparatus 1 according to the first to fourth embodiments includes: the vegetation index computing section 22 that obtains the vegetation information using a captured image of vegetation; the reference vegetation information acquisition section (reference value calculation section 25) that obtains reference vegetation information (reference value Vref) related to a specific environmental stress; and the difference computing section 26 that acquires difference information between the vegetation information and the reference vegetation information related to the specific environmental stress.

This information generation apparatus 1 can obtain the difference between the vegetation information acquired from the captured image of the district to be measured with the certain state of vegetation assumed as a reference and the reference vegetation information. This difference enables the information generation apparatus 1 to evaluate a stress state on the vegetation in comparison with a reference state.

It is noted that the reference vegetation information acquired in advance is often used.

Furthermore, the difference information generated by the difference computing section 26 may either indicate a quantitative numeric value or indicate only a magnitude relationship such as positive/negative. The difference information may be a value that indicates the presence of a stress in a case in which the value is positive and that indicates stress-free in a case in which the value is negative.

In other words, the difference information may indicate presence/absence or degree of the stress.

The information generation apparatus 1 according to the first to fourth embodiments includes the image acquisition section 21 that acquires captured image data by an external imaging apparatus.

Examples of the external apparatus are supposed to include the air vehicle 200 mounting therein the imaging apparatus 250, the fixed point camera, and the camera owned by a person.

Receiving images transmitted from these imaging apparatuses over wired transmission or wireless transmission or reading images from a storage medium enables the information generation apparatus 1 to acquire the captured images of the vegetation in the farm field. Acquiring the captured images as objects to be processed enables the computer apparatus 100 or the like to perform processes as the information generation apparatus 1.

The information generation apparatus 1 according to the first to third embodiments includes, for the captured image data acquired by the image acquisition section 21, the division acquisition section 24 that acquires the division information PI for discriminating a captured image indicating the vegetation information in the state of being free of the specific environmental stress from a captured image indicating vegetation information in the state of being likely to have the specific environmental stress.

It is necessary to discriminate whether the image acquired by the image acquisition section 21 is the image of the reference district Aref or the image of the district to be measured A.

To meet the need, position information, time information, manually input designation information, or the like is received as the division information so that the images can be discriminated. This enables the information generation apparatus 1 to correctly handle the acquired images to generate the stress information.

The information generation apparatus 1 according to the first to third embodiments determines the vegetation information obtained from the captured image indicating the vegetation information in the state of being free of the specific environmental stress on the basis of the division information PI, and obtains the reference vegetation information (reference value Vref) using the determined vegetation information.

This enables the information generation apparatus 1 to accurately determine the reference vegetation information from the vegetation information in the state of being free of the specific environmental stress. In other words, the information generation apparatus 1 can calculate the reference value Vref using the vegetation index image file Ref_P of the reference district Aref.

The information generation apparatus 1 according to the second embodiment includes, for the captured image data acquired by the image acquisition section 21, the image division section 30 that divides the captured image data into the captured image indicating vegetation information in the state of being free of the specific environmental stress and the captured image indicating vegetation information in the state of being likely to have the specific environmental stress.

In other words, in the case of the second embodiment, the image file (M1, M2, or the like) acquired by the image acquisition section 21 contains a mixture of the images of the reference district Aref and the images of the district to be measured A (A1, A2, or the like). In the case in which one captured image contains a mixture of the image of the reference district Aref and the image of the district to be measured A in this way, the images of those districts are divided and extracted.

This enables the information generation apparatus 1 to correctly handle the acquired images to generate the stress information.

The information generation apparatus 1 according to the third embodiment is configured to calculate the reference vegetation information (reference value Vref) relative to the vegetation information in the state of being likely to have the specific environmental stress by using the vegetation information obtained from the captured image in the state of being free of the specific environmental stress that is determined to be identical in the time zone to the captured image used for obtaining the vegetation information in the state of being likely to have the specific environmental stress.

Selecting the vegetation index image file Ref_P in the light of the time zone as in the case of the third embodiment enables the information generation apparatus 1 to calculate the reference value Vref based on the captured image in the same time zone as that of the vegetation index image file M1_P, M2_P, or the like. Since this can be obtained as the reference vegetation information in the case of setting generally identical the environmental conditions other than the specific environmental stress which is, for example, the PRI values, the obtained difference image files M1_DP, M2_DP, and the like serve as information appropriately expressing the specific environmental stress. In other words, it is possible to improve accuracy of measurement information associated with the specific environmental stress.

It is noted that the information generation apparatus 1 according to the first and second embodiments can similarly achieve highly accurate measurement since the reference value Vref can be basically calculated using the image in the same time zone.

The information generation apparatus 1 according to the fourth embodiment includes the instruction section (irrigation instruction section 35) that issues an instruction to change the farm field into the state of being free of the specific environmental stress or the state of being likely to have the specific environmental stress. In other words, the information generation apparatus 1 can change a certain farm field into the state of being likely to have the water stress or the state of being free of the water stress by controlling the irrigation installation.

This enables the information generation apparatus 1 to set even the same district into the state of being free of the specific environmental stress or the state of being likely to have the specific environmental stress.

In the information generation apparatus 1 according to the first to fourth embodiments, the difference computing section 26 generates image information (difference image file M1_DP or the like) serving as the difference information, and the information generation apparatus 1 according to the first to fourth embodiments includes then image output section 28 that outputs this image information.

Outputting the image information as images makes it possible to provide information that is easy for a farm staffer to visually understand and to recognize the environmental stress.

Furthermore, in the information generation apparatus 1 according to the first to fourth embodiments, the reference vegetation information acquisition section (reference value calculation section 25) obtains the reference vegetation information (reference value Vref) using the vegetation information acquired by the vegetation index computing section 22 from the captured image of the vegetation in the state of being free of the specific environmental stress.

This information generation apparatus 1 can obtain the reference value Vref with the state of being free of the specific environmental stress which is, for example, the water stress assumed as a reference, and obtain the difference between the vegetation information acquired from the captured image of the district in which the specific environmental stress is likely to occur and the reference value Vref.

A program according to the embodiments of the present invention is a program causing the CPU 51 in the computer apparatus 100 to execute: a vegetation information computing process for obtaining vegetation information using a captured image of vegetation; a reference vegetation information acquisition process for obtaining reference vegetation information related to a specific environmental stress; and a difference acquisition process for acquiring difference information between the vegetation information and the reference vegetation information.

More specifically, the program according to the embodiments is the program causing the CPU 51 in the computer apparatus 100 to execute: the vegetation information computing process for obtaining the vegetation information using the captured image of the vegetation; the reference vegetation information acquisition process for obtaining the reference vegetation information associated with the vegetation information in the state of being free of the specific environmental stress; and the difference acquisition process for acquiring the difference information between the vegetation information acquired from the captured image of the vegetation in the state of being likely to have the specific environmental stress and the reference vegetation information as information associated with an environmental stress.

In other words, the program according to the embodiments is the program causing the computer 100 to execute the processes of FIGS. 5 and 6 (or processes in FIG. 9 or 12).

Such a program facilitates realizing the information generation apparatus 1 according to the embodiments.

In addition, such a program can be stored in a recording medium embedded in an apparatus such as the computer apparatus, a ROM within a microcomputer that has a CPU, or the like in advance. Alternatively, the program can be saved (stored) in a removable recording medium such as a semiconductor memory, a memory card, an optical disk, a magneto-optical disk, or a magnetic disk either temporarily or permanently. Furthermore, such a removable recording medium can be provided as so-called package software.

Moreover, such a program can be installed from the removable recording medium into a personal computer or the like, or can be downloaded from a download website via a network such as a LAN or the Internet.

It is noted that the effects described in the present specification are given as an example only, and the effects are not limited to those described in the present specification and may contain other effects.

It is noted that the present technique can be configured as follows.

(1) An information generation method including:
a vegetation information acquisition procedure of acquiring vegetation information using an imaging signal of vegetation; and
a difference acquisition procedure of acquiring difference information between the vegetation information and reference vegetation information related to a specific environmental stress.

(2) The information generation method according to (1), in which
the vegetation information acquisition procedure includes obtaining vegetation information associated with a reference district set into a state of being free of the specific environmental stress from an imaging signal of the reference district, and obtaining vegetation information associated with a district to be measured set into a state of being likely to have the specific environmental stress from an imaging signal of the district to be measured, and
as a reference vegetation information acquisition procedure, acquiring the reference vegetation information using the vegetation information associated with the reference district, and
the difference acquisition procedure includes performing computation of a difference between the vegetation information associated with the district to be measured and the reference vegetation information.

(3) The information generation method according to (2), in which
the reference vegetation information acquisition procedure includes
calculating the reference vegetation information used to perform the computation of the difference between the vegetation information associated with the district to be measured and the reference vegetation information by using vegetation information obtained from an imaging signal of the reference district that is determined to be identical in a time zone to the imaging signal used for obtaining the vegetation information associated with the district to be measured.

(4) The information generation method according to (2), in which
the vegetation information acquisition procedure includes obtaining vegetation information from a first imaging signal indicating the district to be measured imaged when the district to be measured is set into the state of being free of the specific environmental stress, and obtaining vegetation information from a second imaging signal indicating the district to be measured imaged when the district to be measured is set into the state of being likely to have the specific environmental stress, the reference vegetation information acquisition procedure includes calculating the reference vegetation information using the vegetation information obtained from the first imaging signal, and the difference acquisition procedure includes performing the computation of the difference between the vegetation information obtained from the second imaging signal and the reference vegetation information.

(5) The information generation method according to any one of (1) to (4) and according to claim 1, in which
the imaging signal includes a captured image.

(6) The information generation method according to any one of (1) to (5), in which
the difference acquisition procedure includes generating image information serving as the difference information.

(7) The information generation method according to any one of (2) to (4), in which
the reference vegetation information acquisition procedure includes
calculating an average value of vegetation information in the state of being free of the specific environmental stress in calculating the reference vegetation information.

(8) The information generation method according to any one of (1) to (7), in which
the specific environmental stress includes any one of a water stress, a low-temperature stress, a high-temperature stress, a drying stress, a stress caused by a shortage of carbon dioxide, or a nitrogen stress.

(9) The information generation method according to any one of (1) to (8), in which
the vegetation information includes any one of a PRI, a magnitude of chlorophyll fluorescence, a chlorophyll fluorescence index, or a state transition reflectance.

(10) An information generation apparatus including:
a vegetation information acquisition section that acquires vegetation information using an imaging signal of vegetation; and
a difference acquisition section that acquires difference information between the vegetation information and reference vegetation information related to a specific environmental stress.

(11) The information generation apparatus according to (10), further including
a reference vegetation information acquisition section that obtains the reference vegetation information using vegetation information acquired from an imaging signal of the vegetation in a state of being free of the specific environmental stress.

(12) The information generation apparatus according to (10) or (11), further including
an image acquisition section that acquires captured image data as an imaging signal by an external imaging apparatus.

(13) The information generation apparatus according to (12), including,
for the captured image data acquired by the image acquisition section,
a division acquisition section that acquires division information for discriminating a captured image indicating the vegetation information in the state of being free of the specific environmental stress from a captured image indicating vegetation information in a state of being likely to have the specific environmental stress.

(14) The information generation apparatus according to (13), in which
the reference vegetation information acquisition section determines vegetation information obtained from the captured image indicating the vegetation information in the state of being free of the specific environmental stress on a basis of the division information, and obtains the reference vegetation information using the determined vegetation information.

(15) The information generation apparatus according to (12), including,
for the captured image data acquired by the image acquisition section,
an image division section that divides the captured image data into a captured image indicating vegetation information in the state of being free of the specific environmental stress and a captured image indicating vegetation information in a state of being likely to have the specific environmental stress.

(16) The information generation apparatus according to (11), in which
the reference vegetation information acquisition section calculates the reference vegetation information relative to vegetation information in a state of being likely to have the specific environmental stress by using vegetation information obtained from an imaging signal in the state of being free of the specific environmental stress, the imaging signal being determined to be identical in a time zone to an imaging signal used for obtaining the vegetation information in the state of being likely to have the specific environmental stress.

(17) The information generation apparatus according to any one of (10) to (16), including
an instruction section that issues an instruction to change a farm field into a state of being free of the specific environmental stress or a state of being likely to have the specific environmental stress.

(18) The information generation apparatus according to any one of (10) to (17), including
an instruction section that controls environmental stress variable installation on a basis of the difference information acquired by the difference acquisition section.

(19) The information generation apparatus according to any one of (10) to (18), in which
the difference acquisition section generates image information serving as the difference information, and
the information generation apparatus includes an image output section that outputs the image information.

(20) The information generation apparatus according to (11), in which
the reference vegetation information acquisition section obtains the reference vegetation information using the vegetation information acquired by the vegetation information acquisition section from the imaging signal of the vegetation in the state of being free of the specific environmental stress.

(21) A program causing a computer to execute:
a vegetation information computing process obtaining vegetation information using an imaging signal of vegetation; and
a difference acquisition process obtaining difference information between the vegetation information and reference vegetation information related to a specific environmental stress.

REFERENCE SIGNS LIST

1 Information generation apparatus, 10 Irrigation controller, 11, 11-R, 11-1, and 11-2 Irrigation setting valve (valve), 12, 12-R, 12-1, and 12-2 Irrigation channel, 21 Image acquisition section, 22 Vegetation index computing section, 23 Vegetation index buffer, 24 Division acquisition section, 25 Reference value calculation section, 26 Difference computing section, 27 Output buffer, 28 Image output section, 29 Output data generation section, 30 Image division section, 31 Imaging time extraction section, 32 Time synchronization section, 33 Input section, 35 Irrigation instruction section, 51 CPU, 52 ROM, 53 RAM, Aref Reference district, A1, A2, A3, and A4 District to be measured, 100 Computer apparatus, 200 Air vehicle, 250 Imaging apparatus,

The invention claimed is:

1. An information generation method comprising:
a vegetation information acquisition procedure of acquiring a first vegetation image at a first wavelength and a second vegetation image at a second wavelength as an imaging signal of vegetation, wherein the vegetation information acquisition procedure includes obtaining, at predetermined intervals, reference vegetation image information, which is associated with a reference district set into a state of being free of a specific environmental stress from an imaging signal of the reference district, the reference vegetation image information comprising a reference vegetation index image related to the specific environmental stress;
a vegetation image indexing procedure wherein a determined vegetation index image is determined based on the first and second vegetation images;
a difference acquisition procedure of acquiring difference information regarding a difference between vegetation image information comprising the determined vegetation index image and the reference vegetation image information; and
an automated irrigation control procedure of automatically controlling a valve that regulates a quantity of irrigation based on the difference information,
wherein the determined vegetation index image is determined by generating a photochemical reflectance value for each pixel of the first and second vegetation images as a vegetation index image,
wherein image data about the photochemical reflectance value of each pixel serves as the vegetation index image, and
wherein the first vegetation image and the second vegetation image are acquired from a position above a first farm field, and wherein the reference vegetation image information is obtained, at predetermined intervals, from a position above a second farm field.

2. The information generation method according to claim 1, wherein
the vegetation information acquisition procedure includes obtaining the vegetation image information, which is associated with a district to be measured set into a state of being likely to have the specific environmental stress from an imaging signal of the district to be measured, and
the information generation method includes a reference vegetation image information acquisition procedure of acquiring the reference vegetation image information using the vegetation image information associated with the reference district, and
the difference acquisition procedure includes performing computation of a difference between the vegetation image information associated with the district to be measured and the reference vegetation image information.

3. The information generation method according to claim 2, wherein
the reference vegetation image information acquisition procedure includes
calculating the reference vegetation image information used to perform the computation of the difference between the vegetation image information associated with the district to be measured and the reference vegetation image information by using vegetation image information obtained from an imaging signal of the reference district that is determined to be in a same time zone as the imaging signal used for obtaining the vegetation image information associated with the district to be measured.

4. The information generation method according to claim 2, wherein
the vegetation information acquisition procedure includes obtaining first vegetation image information from a first imaging signal indicating the district to be measured imaged when the district to be measured is set into the state of being free of the specific environmental stress, and obtaining second vegetation image information from a second imaging signal indicating the district to be measured imaged when the district to be measured is set into the state of being likely to have the specific environmental stress,
the reference vegetation information acquisition procedure includes calculating the reference vegetation image information using the vegetation image information obtained from the first imaging signal, and
the difference acquisition procedure includes performing the computation of the difference between the vegetation image information obtained from the second imaging signal and the reference vegetation image information.

5. The information generation method according to claim 1, wherein
the imaging signal includes a captured image.

6. The information generation method according to claim 1, wherein the first vegetation image is produced using 531 nm wavelength light, and wherein the second vegetation image is produced using 570 nm wavelength light.

7. The information generation method according to claim 1, further comprising:
a reference vegetation information acquisition procedure of calculating an average value of vegetation image information in the state of being free of the specific environmental stress as the reference vegetation image information.

8. The information generation method according to claim 1, wherein
the specific environmental stress includes any one of a water stress, a low-temperature stress, a high-temperature stress, a drying stress, a stress caused by a shortage of carbon dioxide, or a nitrogen stress.

9. The information generation method according to claim 1, wherein the first vegetation image is produced using light of wavelengths between 691 nm and 759 nm.

10. An information generation apparatus comprising:
a vegetation information acquisition section that acquires vegetation image information at a first wavelength and a second vegetation image at a second wavelength as an imaging signal of vegetation, wherein the vegetation information acquisition procedure includes obtaining, at predetermined intervals, reference vegetation image information, which is associated with a reference district set into a state of being free of a specific environmental stress from an imaging signal of the reference district, the reference vegetation image information comprising a reference vegetation index image related to the specific environmental stress;

a vegetation image indexing section that determines a vegetation index image based on the first and second vegetation images;

a difference acquisition section that acquires difference information regarding a difference between vegetation image information comprising the determined vegetation index image and reference vegetation image information comprising the reference vegetation index image; and an automated irrigation control section that automatically controls a valve that regulates a quantity of irrigation based on the difference information, wherein the determined vegetation index image is determined by generating a photochemical reflectance value for each pixel of the first and second vegetation images as a vegetation index image, wherein image data about the photochemical reflectance value of each pixel serves as the vegetation index image, and wherein the first vegetation image and the second vegetation image are acquired from a position above a first farm field, and wherein the reference vegetation image information is obtained, at predetermined intervals, from a position above a second farm field.

11. The information generation apparatus according to claim 10, further comprising:

a reference vegetation information acquisition section that obtains the reference image vegetation information using vegetation image information acquired from an imaging signal of vegetation in a state of being free of the specific environmental stress.

12. The information generation apparatus according to claim 10, wherein the first vegetation image is produced using 531 nm wavelength light, and wherein the second vegetation image is produced using 570 nm wavelength light.

13. The information generation apparatus according to claim 12, further comprising:

for the captured image data acquired by the image acquisition section, a division acquisition section that acquires division information for discriminating a captured image indicating the vegetation in the state of being free of the specific environmental stress from a captured image indicating vegetation in a state of being likely to have the specific environmental stress.

14. The information generation apparatus according to claim 13, wherein the reference vegetation information acquisition section obtains the reference vegetation image information using the determined vegetation information.

15. The information generation apparatus according to claim 12, further comprising:

for the captured image data acquired by the image acquisition section, an image division section that divides the captured image data into a captured image indicating vegetation image information in the state of being free of the specific environmental stress and a captured image indicating vegetation image information in a state of being likely to have the specific environmental stress.

16. The information generation apparatus according to claim 11, wherein the reference vegetation information acquisition section calculates the reference vegetation image information relative to vegetation image information in a state of being likely to have the specific environmental stress by using vegetation image information obtained from an imaging signal in the state of being free of the specific environmental stress, the imaging signal being determined to be in a same time zone as an imaging signal used for obtaining the vegetation image information in the state of being likely to have the specific environmental stress.

17. The information generation apparatus according to claim 10, further comprising:

an instruction section that issues an instruction to change a farm field into a state of being free of the specific environmental stress or a state of being likely to have the specific environmental stress.

18. The information generation apparatus according to claim 10, further comprising:

an instruction section that controls an environmental stress variable installation on a basis of the difference information acquired by the difference acquisition section.

19. The information generation apparatus according to claim 10, wherein the difference acquisition section generates image information serving as the difference information, and the information generation apparatus includes an image output section that outputs the image information.

20. A non-transitory computer readable medium comprising computer program code that, when executed by a processor, causes the processor to execute:

a vegetation information computing process of obtaining vegetation image information at a first wavelength and a second vegetation image at a second wavelength as an imaging signal of vegetation, wherein the vegetation information acquisition procedure includes obtaining, at predetermined intervals, reference vegetation image information, which is associated with a reference district set into a state of being free of a specific environmental stress from an imaging signal of the reference district, the reference vegetation image information comprising a reference vegetation index image related to the specific environmental stress;

a vegetation image indexing process of determining a vegetation index image based on the first and second vegetation images;

a difference acquisition process of obtaining difference information regarding a difference between vegetation image information comprising the determined vegetation index image and reference vegetation image information comprising the reference vegetation index image; and an automated irrigation control procedure of automatically controlling a valve that regulates a quantity of irrigation based on the difference information, wherein the determined vegetation index image is determined by generating a photochemical reflectance value for each pixel of the first and second vegetation images as a vegetation index image, wherein image data about the photochemical reflectance value of each pixel serves as the vegetation index image, and wherein the first vegetation image and the second vegetation image are obtained from a position above a first farm field, and wherein the reference vegetation image information is obtained, at predetermined intervals, from a position above a second farm field.

\* \* \* \* \*